United States Patent
Pinsky et al.

[11] Patent Number: 6,150,812
[45] Date of Patent: Nov. 21, 2000

[54] DETECTION OF ELECTROMAGNETIC FIELDS AS A DETERMINANT OF AN EVENT

[75] Inventors: Carl Pinsky, Winnipeg; Frank S. LaBella, Oakbank, both of Canada

[73] Assignee: Fermion Inc., Kelowna, Canada

[21] Appl. No.: 08/696,880

[22] PCT Filed: Feb. 20, 1995

[86] PCT No.: PCT/CA95/00082

§ 371 Date: Oct. 18, 1996

§ 102(e) Date: Oct. 18, 1996

[87] PCT Pub. No.: WO95/23339

PCT Pub. Date: Aug. 31, 1995

[30] Foreign Application Priority Data

Feb. 21, 1994 [GB] United Kingdom .................. 9403245

[51] Int. Cl.[7] .......................... G01N 27/72; G01N 33/48; G01R 33/035; G01R 33/07
[52] U.S. Cl. .......................... 324/261; 204/400; 324/71.1; 324/224; 324/248; 324/251; 324/345; 324/425; 600/409
[58] Field of Search ...................................... 324/300, 309, 324/344, 345, 204, 224, 225, 228, 234, 239, 244, 248, 251, 260, 261, 71.1, 71.2, 425; 204/400, 403, 404; 600/407, 409

[56] References Cited

U.S. PATENT DOCUMENTS 4,121,288 10/1978 Hickam .................................. 324/213 X
4,724,390 2/1988 Rauscher et al. ........................ 324/344
4,769,601 9/1988 Herrick .................................... 324/300
5,087,873 2/1992 Murphy et al. ........................ 324/71.2
5,201,311 4/1993 Bottomley et al. ................. 324/309 X

FOREIGN PATENT DOCUMENTS 2001580 1/1990 Japan.
4238281 8/1992 Japan.

OTHER PUBLICATIONS

Bellingham et al; Squid Technology Applied to the Study of Electrochemical Corrosion, IEEE Transactions on Magnetics, vol. Mag–23, No. 2 Mar. 1987, pp. 477–479.

Hoenig et al; "Biomagnetic Multichannel System . . . Operating in a Shielded Room", Cryogenics, vol. 29, Aug. 1989, pp. 809–813.

Misra et al; NDE Applications of Squid Magnetometry to Electrochemical Systems, IEEE Transactions on Magnetics, vol. 27, No. 2, Mar. 1991, pp. 3245–3247.

*Primary Examiner*—Gerard Strecker
*Attorney, Agent, or Firm*—Sim & McBurney

[57] ABSTRACT

Method and apparatus for detecting or analyzing chemical reactions, such as an enzyme reaction, and other events in which electron translation is accompanied by photon emission utilizing a magnetometer probe to detect a change in electromagnetic field strength as a characterization of the event. The event may be of unknown cause and a recorded time course of the change in electromagnetic field strength may be compared with known events to determine the cause of the unknown cause event.

11 Claims, 23 Drawing Sheets

INSTRUMENTATION, BLOCK DIAGRAM

INSTRUMENTATION, BLOCK DIAGRAM

DETECTION OF ELECTROMAGNETIC FIELDS AS A DETERMINANT OF AN EVENT

REFERENCE TO RELATED APPLICATION

This application is a U.S. National Phase filing pursuant to 35 to USC 371 from PCT/CA95/00082 filed Feb. 20, 1995.

FIELD OF INVENTION

The present invention relates to the detection of electromagnetic fields produced by certain events, such as chemical reaction, as well as for a device for maintaining the generation of such electromagnetic fields.

BACKGROUND TO THE INVENTION

The motion of electrons within a single isolated atom or molecule generates electromagnetic fields which can be detected external to the boundaries of the atom or molecule. The magnitude and frequency of such external fields depends mainly upon the following factors:

(i) the angular momentum of the electron as it spins on its axis (=electron spin angular momentum), (ii) the angular momentum of the electron as it moves in quasicircular orbital paths around the nucleus (=electron orbital momentum), (iii) the quantized energy states of the electron orbital paths and angular spin velocities, (iv) intraatomic and intramolecular interactions between electron motions as governed by Lenz's law, (v) rate of individual transitions between quantized energy states and the frequency of transitional events, (vi) interactions between electron orbital and spin angular moments and nuclear magnetic moments, and (vii) intensity, frequency and direction of externally imposed magnetic fields.

The electromagnetic fields generated by electron motion within atoms or molecules are accompanied by the simultaneous emission of photons whose energies are characteristic of the frequencies of the associated atomically- or molecularly-generated external magnetic fields. The range of atomic and molecular electromagnetic frequencies extends from microwave to ultraviolet energies.

SUMMARY OF INVENTION

As described in more detail below, the present invention utilizes, among several related and exploitable phenomena, the electromagnetic consequences of chemical interactions between molecules, and between molecules and atoms, to characterize types of reactions and identify the reactant chemicals by (i) direct magnetometric detection of magnetic fields external to the reactants and by (ii) magnetometric detection of magnetic domain configurations that are set up both by microwave photons and by propagating microwave electromagnetic fields in substances which surround the reactants and which behave as transducers of high frequency atomic/molecular magnetic field oscillations into magnetic domain fluctuations at much lower frequencies, e.g. 0 to $10^4$ hertz (Hz).

The transducing substances can be in gaseous, liquid or solid phases and are weakly ferromagnetic over at least some range of imposed microwave energies. Transducing substances which are strongly ferromagnetic by virtue of iterative metallic crystal ionic bonds exhibit the transduction-necessary weak ferromagnetism mode as a surface phenomenon of only several atoms thickness, consistent with the observed ability of thin films of reactant systems to increase the sensitivity and reproducibility of the device provided herein.

Similar frequency conversion mechanisms inherent in ferromagnetic, weakly ferromagnetic and paramagnetic micro- and nanostructures and systems (e.g. atoms, molecules, nano- and microcavities and stereosurfaces, nano-, micro- and ultrafine wires), are utilized to enable detection, by conventional magnetometry, of chemically- and intraatomically-generated electromagnetic and quantum (photon) phenomena. Utilizing the same energy-transduction and magnetometry technology, quantum particulate and propagating high-frequency electromagnetic emissions released during radioactive decay are exploited to detect and measure gamma and beta (+) and (−) emission from weak radioactive sources.

The invention, therefore, represents a universal detector of circulating electronic currents in all forms of matter whose dimensions may range from macroscopic to ultrananoscopic and of translation and quantum mechanical axial spin of electrons in all such matter. The present invention thus constitutes a practical, reliable, transducer of the magnetic intra- and extra-atomic consequences of interactions between electron movement and propagating electromagnetic fields over an extremely wide range of field strengths and frequencies.

The present invention does not require any technically-generated external magnetic fields, either steady or time-variant, but includes simple high-permeability ferromagnetic shielding as a means to reduce the ubiquitous geomagnetic field and its inherent fluctuations. The same shielding serves, over a wide range of frequencies, to reduce the effects of stray magnetic fields of non-geomagnetic origin and is also an important component of the frequency-changing transduction mechanism whereby electromagnetic energies originating at atomic frequencies promote the formation of ferromagnetic or quasiferromagnetic domains detectable by conventional magnetometry.

Accordingly, in one aspect of the present invention, there is provided a method of detection of an event in which electron translation is accompanied by photon emission, which comprises detecting a change in electromagnetic field strength caused by the event. Such event may comprise a chemical reaction, a molecular interaction and/or a change of state of matter.

Such event may be of known cause and a time course of the change in electromagnetic field strength, i.e. the changes in electromagnetic field strength over time, may be recorded as a characterization of the event.

Alternatively, the event may be of unknown cause. A time course of the change of electromagnetic field strength is recorded and compared with predetermined time courses of known events in which electron translation is accompanied by photon emission to determine the cause of the unknown cause event.

One specific application of the procedure of the invention is to determine the electromagnetic consequences of enzyme reactions by detection and measurement of changes in the electromagnetic field strength at temperatures which are optimum for the enzyme reaction of interest.

The recordal of the change of electromagnetic field strength may be effected in any convenient manner which permits the characteristic time course of the event to be provided and, if desired, compared with known prior-recorded time courses. Such analysis may be effected by FAST FOURIER TRANSFORM (FFT) procedures and may be enhanced, augmented and/or assisted by other forms of signal analysis, such as pattern recognition and/or wave trend forecasting.

The change in electromagnetic field strength caused by the event may be detected in any desired manner. As described in more detail herein, the detection may be made by a magnetometer probe capable of generating an electrical signal in response to an electromagnetic field with the electrical signal being of a strength proportional to the strength of the electromagnetic field and the recording of the change in electromagnetic field strength then is made by recording the time course of the electrical signal produced by the magnetometer.

GENERAL DESCRIPTION OF INVENTION

Figure 1:
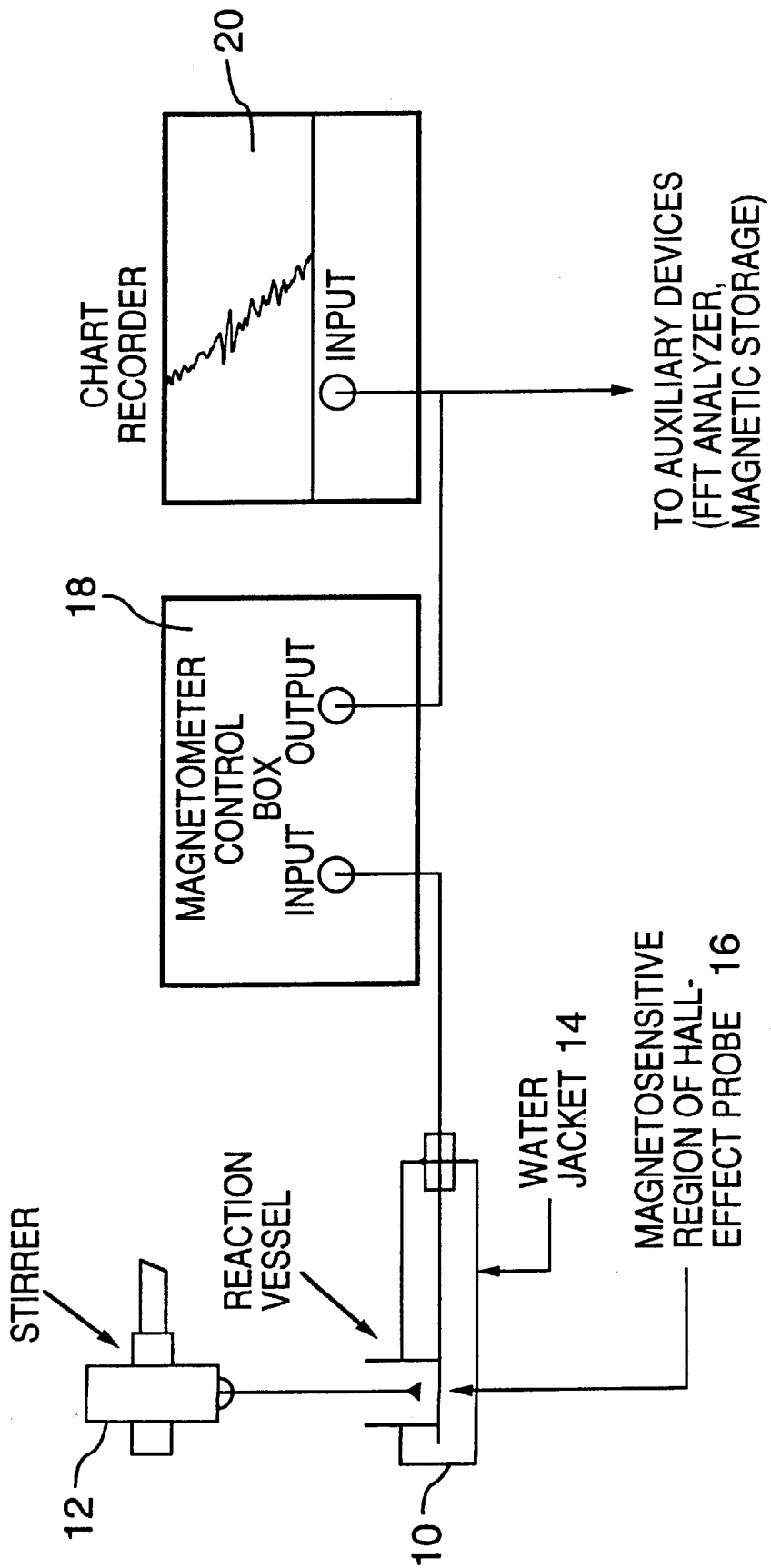
FIG. 1 is a schematic representation of a device provided in accordance with one aspect of the invention.

No net magnetic field at low (e.g. 0 to $<10^4$ Hz) frequency can be recorded, except for very short intervals, from macroscopic aggregates of atoms or molecules at rest. This is because the magnetic moments of the individual atoms or molecules in such a aggregates will on average find orientations whose resultant external magnetic field intensities are for all practical purposes zero. Only by the imposition of an external coercive agency can a macroscopic system in any state of matter including crystalline lattice structures generate detectable net slowly-varying external magnetic fields on other than a stochastic basis. The external coercive agency must be capable of aligning the magnetic moments of a plurality of the atoms or molecules in the aggregate. Past technology and geo/cosmological natural circumstance has relied upon the application of external magnetic or electric fields, electromagnetic radiation (including light) or extremes of heat (at times coupled with mechanical forces) to provide the coercive energy necessary for magnetic alignment.

The present invention is novel and unique in that the quantum dynamic electronic events which accompany chemical reactions are exploited to synchronize the events described in factors (i) through and including (vii) discussed above. The synchronization is initially temporal and will occur in any state of matter or medium in which the chemical reaction(s) occur(s). The temporal synchrony quickly leads to spatial alignment of atomic or molecular moments, since the electric and magnetic forces generated by the chemical reaction will interact complexly to reduce and maintain the total free energy of the aggregate to and at a minimum. In this sense, the initial and the maintained synchrony of chemical reaction-driven atomic electronic events substitutes for the ordered interatomic geometrical constraints and interactions which occur in the solid crystalline state of matter and which give rise to magnetization in ferromagnetic substances. Such interatomic or intermolecular ordering, which we designate as "chemical reaction-induced magnetosynchrony" or CRIM, can give rise to the equivalent of enormous applied fields in the material aggregate, e.g. in magnetized iron a submicroscopic domain of $10^{15}$ atoms can have interatomic alignments equivalent to an applied field of $10^3$-T-cm$^{-1}$ (ref. Ha49—The identification and a list of the references appears at the end of the disclosure). In many chemical reactions, the largest single contribution that will be made by CRIM is the quantized change in electron spin state, since the gyromagnetic ratio, g (ratio of electron spin angular momentum to electron orbital momentum), for ferromagnetic substances is characteristic of the spinning electron (ref. Ha49). In this regard, the present invention, while applicable to all categories of chemical reactions and molecular interactions, is especially useful for the detection and analysis of those reactions associated with changes in spin states (quantized energy levels for electrons in different orbits and orbitals) of one or more of the reactants. This detector band analysis is of particular relevance in evaluating the characteristics of enzyme reactions, since many enzyme-substrate interactions can be largely or totally characterized by reaction-driven electron spin phenomena, mainly those of enzyme-substrate interaction-initiated transitions in electron spin state. The present invention discerns such phenomena in the reaction vessel provided herein via simple magnetometery, which requires no application of an external magnetic field and no high-frequency exposure or specialized high-frequency detection system. The present invention does not require low-temperature cryogenic environment for its operation and can be utilized at noncritical laboratory temperatures, usually ranging from about 15° C. to about 40° C., with even greater latitude where desired.

DESCRIPTION OF PREFERRED EMBODIMENT

Referring to FIG. 1, there is illustrated therein a schematic representation of a device for detection of chemical reactions and other molecular interactions, including changes in state of matter. As seen therein, the device includes a reaction vessel 10, which may be equipped with a stirrer 12.

The reaction vessel 10 is equipped with a water jacket 14 to maintain a desired temperature. A magnetometer probe 16 is positioned in the reaction vessel. In a preferred embodiment of this invention, the magnetometer probe is a semiconductor Hall-effect generator. The water jacket 14 provide temperature regulation of the magnetosensitive area of the magnetometer probe 16.

In the specific equipment used to generate the magnetometer charts of FIGS. 2 to 23, the magnetometer probe 16 uses a semiconductor Hall-effect generator with a circular magnetosensitive area of 16 sq. mm. The reaction tube 10 consists of a 20 mm length of borosilicate glass tubing of 4 mm i.d. and is fixed to the magnetosensitive area.

The reaction vessel 10 may be dimensioned to accommodate any desired volume of liquid. In the specific device described above, solution volumes up to 1000 $\mu$L may be added to the reaction tube 10 and volumes as low as 1.0 $\mu$L can be analyzed when presented to the probe or a thin film sandwiched between two thin plastic discs of slightly less than 4 mm in diameter, or other dimension depending on the dimension of the magnetosensitive area of the magnetometer probe.

The use of a thin-film reaction system as just described is highly convenient and yields magnetometer responses that are accurate and rapidly analyzed. Samples and ongoing chemical reactions and interactions can be analyzed according to the invention also when placed in proximity to the magnetosensitive area of the magnetometer probe, even when the location of the sample is outside the water jacket 14.

The magnetometer probe 16 is connected to a magnetometer amplifier and control box 18. For a Hall-effect magnetometer probe, the control box 18 may house a standard Hall-effect amplifier and control system. The control box 18 is connected to a chart recorder 20 or other convenient manner of recording the output from the magnetometer probe.

In the specific experiments detailed herein, the standard Hall-effect amplifier and control system was set to have a maximum working range of sensitivity of 200 microgauss full-scale for display on a laboratory chart recorder. The working output of the magnetometer system was read out on a graph of time vs. magnetic field strength in microgauss (see FIGS. 2 to 23).

Since differing molecular interactions can be expected to produce characteristic time vs. field strength relationships, a FAST FOURIER TRANSFORM (FFT)-assisted spectral analysis of the unprocessed magnetometer output signal may provide information concerning the nature of the molecular interaction(s) proceeding in the reaction vessel, even long before the reaction kinetics have reached equilibrium. The spectral analysis provides a signature frequency spectrum to specific chemical interactions.

The generation of specific frequency spectra in accordance with this aspect of the present invention, enables the identity of an unknown reaction to be determined rapidly and accurately. In Table 1 below, there is listed specific various types of chemical reactions which are amenable to identification by such signature spectra, as well as specific applications of this aspect of the invention in studies on biological, biochemical and biomedical phenomena.

The use of a superconducting quantum-interference detector (SQUID) probe can provide signal-to-noise ratios many orders of magnitude greater than the Hall-effect magnetometer probe described here and may be employed in place thereof. Each improvement in signal-to-noise permits the measurement of chemical interactions with progressively smaller reaction volumes. Thus with the attachment of a SQUID magnetometer probe our invention would be able to analyze chemical reactions in microscopic volumes or at great distances from the reacting substances. The latter facility would permit the present invention to be used to detect, identify and non-invasively analyze, in real time, specific chemical reactions ongoing in the interior of the living body, e.g. in humans. Increases in signal-to-noise ratios and smaller reaction volumes also decrease analysis times, since the FFT virtual-filtering routines have less noise to remove. As a component of the present invention, therefore, a SQUID magnetometer probe provides a non-invasive, rapid, nonconfining method of diagnosing metabolic disease states from without the human body.

Use of a SQUID magnetometer probe in the present invention permits also the detection of electromagnetic fields generated in the microwave ranges during chemical reactions. This in turn permits the present invention to detect and analyze chemical events, taking place in reaction vessels or in the living body, whose activity and specific chemical nature is characterized by microwave radiation in specific regions of the microwave spectrum.

The addition of a simple static or slowly-varying magnetic field generator to the device in conjunction with a SQUID magnetometer permits the present invention to function, under certain conditions, as an electron spin resonance (ESR) spectrometer and thereby discern molecular structure without requiring the chemical sample to be submitted to microwave radiation. One condition where this would obtain is during a chemical reaction involving known or unknown molecular entities. This result is achieved because the waveform of microwave signals from a chemically-reacting molecule in a magnetic field changes with imposed magnetic field strength in unique fashion for individual molecules. Such application of the invention can with convenience be further enhanced by attaching to the magnetometer probe a semiconductor Peltier-effect thermoelectric cooler, with appropriate electronic control system. This facility permits the analysis of chemical structure at cryogenic temperatures, a circumstance which reduces the rotation of protons around single bonds in the molecule of interest, thereby permitting more accurate representation and resolution of molecular conformation. The extension of the invention to provide a nuclear magnetic resonance facility involves merely the addition of the necessary magnetic field coil(s) and control system to the magnetometer probe.

The practical shortest analysis time for the generation of a specific frequency spectrum from a given procedure is approximately ten times the period of the lowest frequency present in the frequency bandwidth chosen for analysis. With the small volumes and reactant concentrations necessary for achieving results using the present invention, this lower limit may approach no more than about one to two minutes. Spectral or other modes of analysis, for example, pattern recognition and waveform trend forecasting, can be accomplished with a user-programmable digital computer which stores the unprocessed signal, the analyzed result and experimental notations on magnetic media. Outputs of all stored modes can be displayed, as chosen, on the computer screen. These outputs can then be compared by visual and statistical means with response patterns previously obtained from known reactions under controlled conditions or derived from theory. Thus, general and specialized libraries of spectral and response pattern data can be built up as the invention is utilized in an individual laboratory or can be compiled from variegated laboratories in several different areas of investigation. An expert system would be available to assist the investigator with the interpretation of results.

DESCRIPTION OF FURTHER APPLICATIONS OF INVENTION

This patent application is concerned with all applications of the principles described herein, for the detection or analysis of chemical reactions, molecular interactions, radioactivity and changes in state of matter, including the formation of plasmas, polymers, spin glasses (ref. Vi77), liquid crystals and phase transitions in gases, liquids, solids (ref. Si82) and colloids constituted from all states of matter.

The present invention, in addition to the specific uses described above, is useful for, the detection and measurement of:

(i) Free radicals, in solution or in gaseous, liquid, sol or gel colloid suspension, whether stationary or in motion relative to the magnetometer probe.

(ii) All chemical entities with unpaired electrons or with asymmetric nuclear magnetic momentum, whether stationary or in motion relative to the magnetometer probe.

(iii) Chemical reactions, especially those in enzymatic pathways, within the living body, by means of a magnetometer probe attachment of suitable shape, size, and adequate sensitivity and signal-to-noise ratio, whether the reaction and molecular interactions under intended observation are the result of ongoing bodily activities in health or disease or are stimulated to CRIM magnetosynchrony by the administration of exogenous substances such as specific substrates for chosen enzyme systems or by the application of electromagnetic energy such as bioluminescence either coherent or noncoherent, coherent light, such as laser energy, electromagnetic fields at any frequency or by ultrasonic, thermal or mechanical energy.

(iv) Chemical reactions and molecular interactions observed in vitro in tissues excised ethically from plants, insects, animals, patients and their controls, in order to distinguish healthy from diseased tissue and under experimental conditions as described above.

(v) Industrial effluent gases, liquids, solids and suspensions, whether colloidal, quasi-colloidal or crudely macroscopic systems.

(vi) Magnetic field patterns to be used in seeking fossil fuels, whether gaseous, liquid or solid; underground water and its variant solute-modified constitutions; underground pollutants, especially those hazardous to underground workers, the hazards to include coal dust, explosive gases and toxic gases; specific rock formations indicating species of ore, fault lines and tectonic formations and hazards, solid or liquid pollutant substances in soil, groundwater and aquifers.

(vii) Electromagnetic field patterns predictive of impending earthquakes.

(viii) Chemical reactions and molecular interactions in oceans, rivers, lakes and reservoirs where analysis or detection of the chemical reactions can yield information concerning ongoing or incipient environmental pollution hazards.

(ix) Chemical reactions and molecular interactions in soil, where analysis or detection of the chemical reactions can yield information concerning the ongoing biochemical activity of soil organisms and concerning ongoing or incipient environmental pollution hazards.

(x) Chemical reactions in industrial processes where on-line information in real time is desired concerning the kinetics and phases of continuous chemical reactions in the ongoing batch or bulk process with the object of automating and regulating the process for optimal productivity and quality. In reactions of all kinds, the ability of the invention to detect and identify intermediates in the total reaction process, in laboratory micro-, bench-top and industrial-scale batches. The present invention, being particularly useful for monitoring the reaction rates and kinetics of polymerization reactions since the formation of polymerizing bond structures generates molecular magnetic domains similar to those found in magnetized mineral and ferrite substances, may also be used for detection and monitoring of polymerization processes.

(xi) Incipient and ongoing ice formation in shipping ports, on rivers and in lakes, on highways, roads and rail lines, on surface vehicles, especially on windscreens and windows and on wings, ailerons, cowling, wheel fittings and other ice hazard-sensitive areas of aircraft and spacecraft.

(xii) The electromagnetic pulse (EMP) which accompanies the detonation of a nuclear device, either fission or fusion type and, by means of the FFT spectral analysis facility of this invention, analysis of the isotopes involved in the fission and/or fusion events.

(xiii) Application of the present invention for measuring or monitoring any of the chemical reactions/ interactions, electromagnetic energies, atomic or nuclear events mentioned in the foregoing that can be monitored from locations technically remote from the magnetosensitive region of the magnetometer probe.

EXAMPLES

The device illustrated in FIG. 1 has been employed in the generation of charts depicting the time course of various reactions carried out in the reaction vessel 10 and these charts are shown in FIGS. 2 to 23. The specific reactions and conditions are outlined in the Figures using certain abbreviations and are tabulated in Table 3 below. Examples of some biochemical pathways identified by the device of FIG. 1 and shown in certain of the FIGS. 2 to 23 are detailed in Table 2 below while specific identification of the experiments depicted by FIGS. 2 to 23 is shown in Table 4 below.

SUMMARY OF THE DISCLOSURE

In summary of this disclosure, the present invention provides a novel method of detecting or analyzing an event, such as a chemical reaction, molecular interaction and/or change of state of matter by detecting a change in electromagnetic field strength. Modifications are possible within the scope of this invention.

REFERENCES (Ha49) Harnwell, G. P. (1949). Principles of Electricity and Electromagnetism. McGraw-Hill, New York.

(Si82) Sinai, Ya G. (1982). Theory of Phase Transitions: Rigorous Results, Pergamon Press, Oxford.

(Vi77) Villain, J. (1977). *J. Phys.* C10: 4793–4803.

TABLE 1

Some Applications of Signature
Spectra and Pattern Analysis

| | |
|---|---|
| A. | Enzyme reactions |
| | 1. Sequential addition of substrates |
| | 2. Mixtures of substrates |
| | 3. Optimization of conditions: Co-factors, ions, metals |
| | 4. Spectra from cells and tissues |
| B. | Molecular interactions |
| | 1. Ligand/receptor |
| | 2. Antigen/antibody |
| | 3. Substrate/enzyme |
| C. | Tissue/cell profiles |
| | 1. Basal conditions or in response to added ligand |
| | 2. Normal vs. disease |
| | 3. Specific frequency spectrum signature |

TABLE 2

Examples of some biochemical pathways that
the inventors have identified by use of
the device described in this document

| Non-NADPH-dependent Substrate | rat liver microsomes | Metabolized by *pig liver chromatin |
|---|---|---|
| histidine | + | ++ |
| histidinol | + | + |
| histamine | + | + |
| adenosine | + | + |
| ornithine | ++ | + |

TABLE 2-continued

Examples of some biochemical pathways that the inventors have identified by use of the device described in this document

| Non-NADPH-dependent Substrate | rat liver microsomes | Metabolized by *pig liver chromatin |
|---|---|---|
| NADPH-dependent | | |
| aminopyrine | + | − |
| aniline | + | − |
| putrescine | + | + |
| testosterone | − | + |
| estradiol | + | − |
| progesterone | + | − |
| cortisol | + | − |
| amitryptyline | + | + |
| fluoxetine | + | + |

Legend:
"+" = Pathway response readily apparent.
"++" = Strong pathway response.
"−" = No response; no evidence for pathway.
* Most of these observations and virtually all in the chromatin are original to our laboratories and can be done with our device, in its present state of development, in a total of no more than 10 experimenter-hours. Currently available state-of-the-art analytical systems would likely require a minimum of 2500 experimenter-hours to accomplish the same results.

TABLE 3

Abbreviations on Figures
(Numbers in parentheses indicate vol in µl concentrations of stock solutions added)

| | |
|---|---|
| AD = | adenosine (0.2 mM) |
| AN = | aniline (0.2 mM) |
| AP = | aminopyrine (0.2 mM) |
| B = | 0.1 M TRIS-PO$_4$ buffer |
| CHROM = | chromatin from pig liver nuclei (I mg protein/ml) |
| CORT = | cortisol (I µM) |
| EST = | β-estradiol (1 µM) |
| GBT = | glass bottom tube |
| HA = | histamine (0.2 mM) |
| HD = | histidine (0.2 mM) |
| HOL = | histidinol (0.2 mM) |
| NADPH = | reduced nicotinamide adenine dinucleotide phosphate (0.5 mM) |
| ORN = | ornithine (0.2 mM) |
| PBT = | probe is bottom of tube |
| PGT = | flat-bottom glass tube on probe |
| PL = | phospholipid substrate |
| PLase = | bee venom phospholipase |
| PLN = | pig liver nuclei (1 mg protein/ml) |
| PROG = | progesterone (1 µM) |
| PU = | putrescine (0.2 mM) |
| Regen = | NADPH regeneration system: glucose-6-phosphate, glucose-6-phosphate dehydrogenase, NADP |
| RLM = | rat liver microsomes (1 mg protein/ml) |
| TEST = | testosterone (1 µM) |

TABLE 4

Legends to Figures

Figure 2:
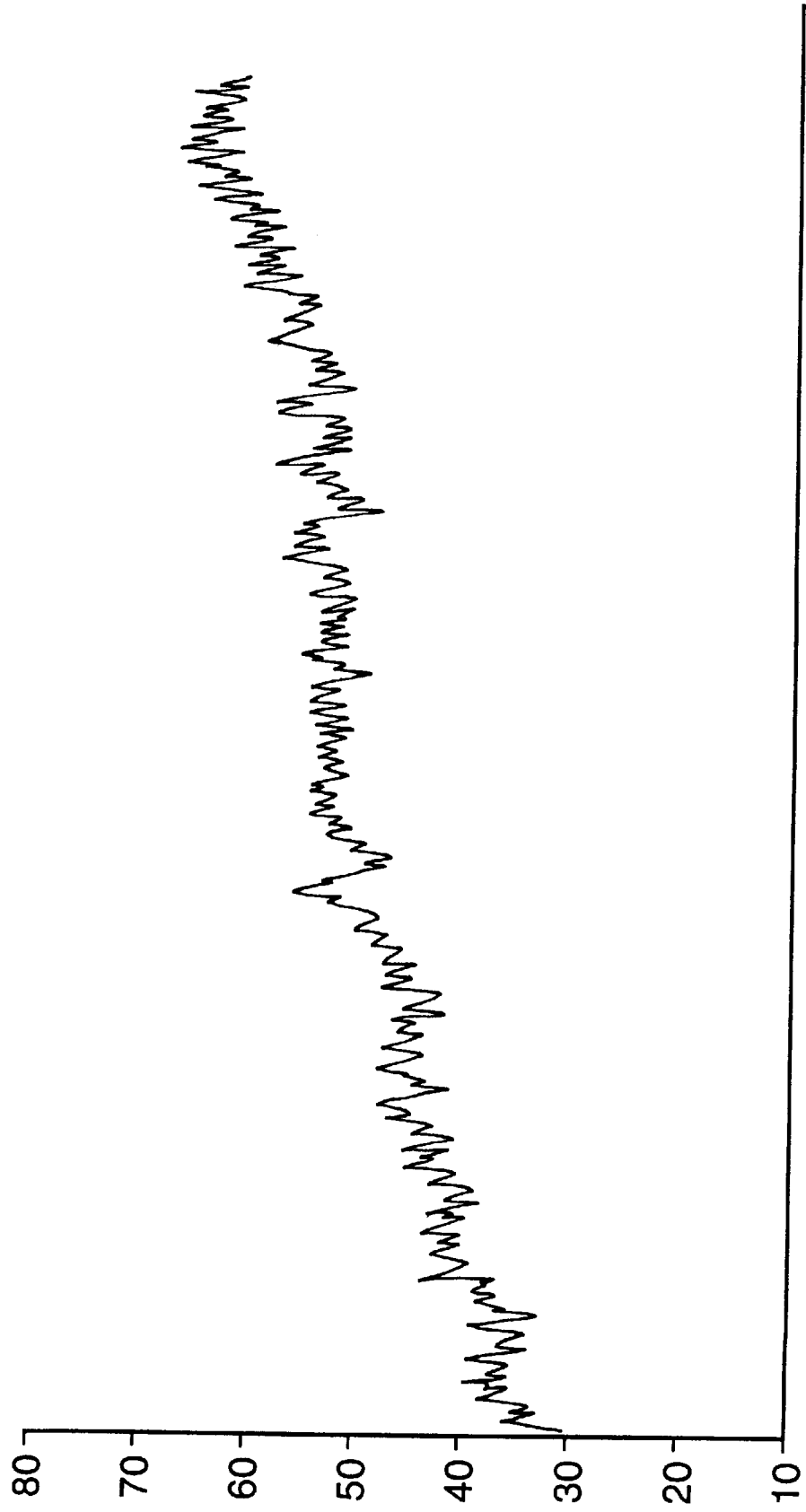
FIGS. 2 to 23 are a series of actual charts generated using the apparatus of FIG. 1 illustrating same typical reactions examined, showing the experimental conditions employed and the results obtained.
Figure 3:
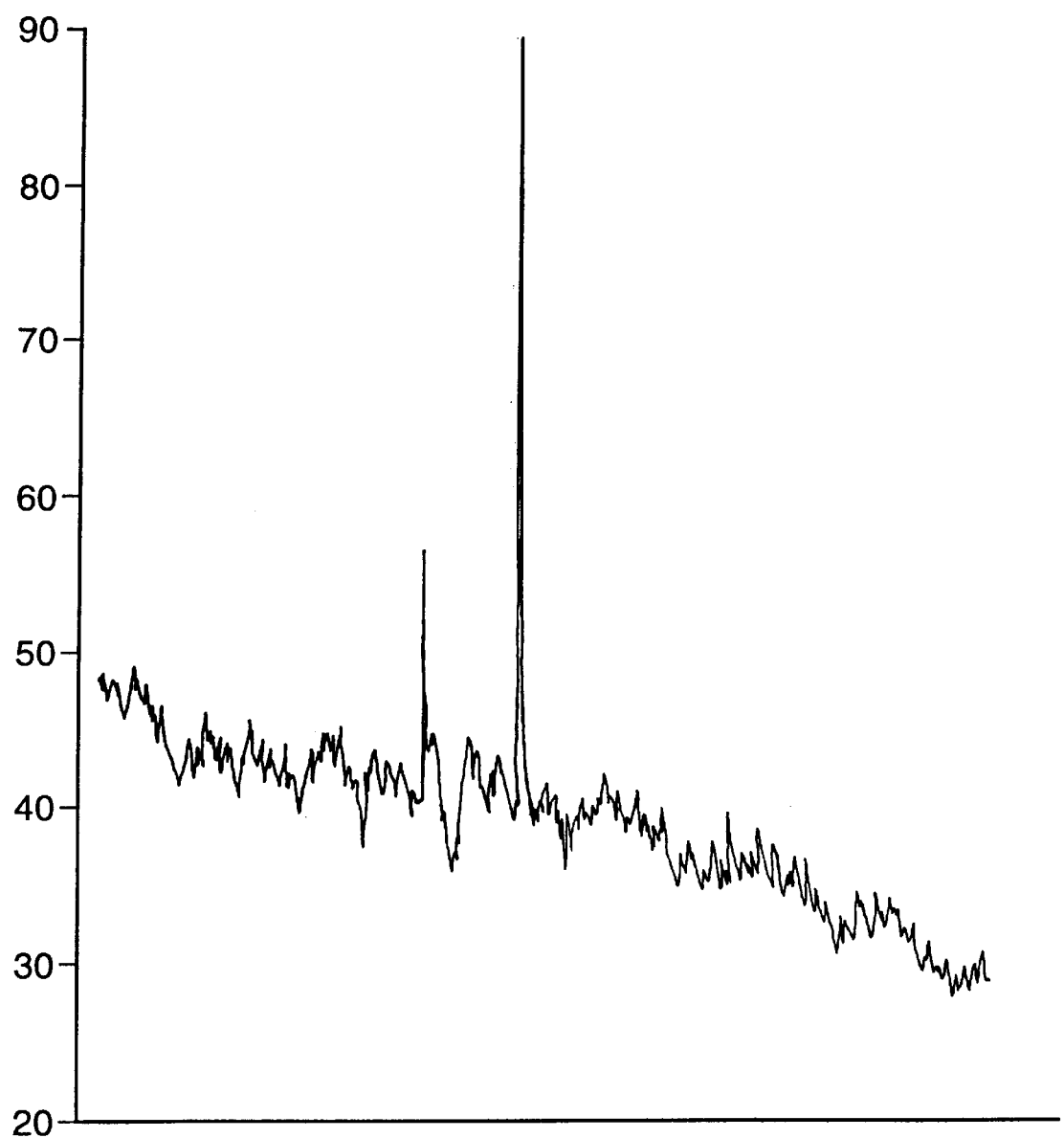
Figure 4:
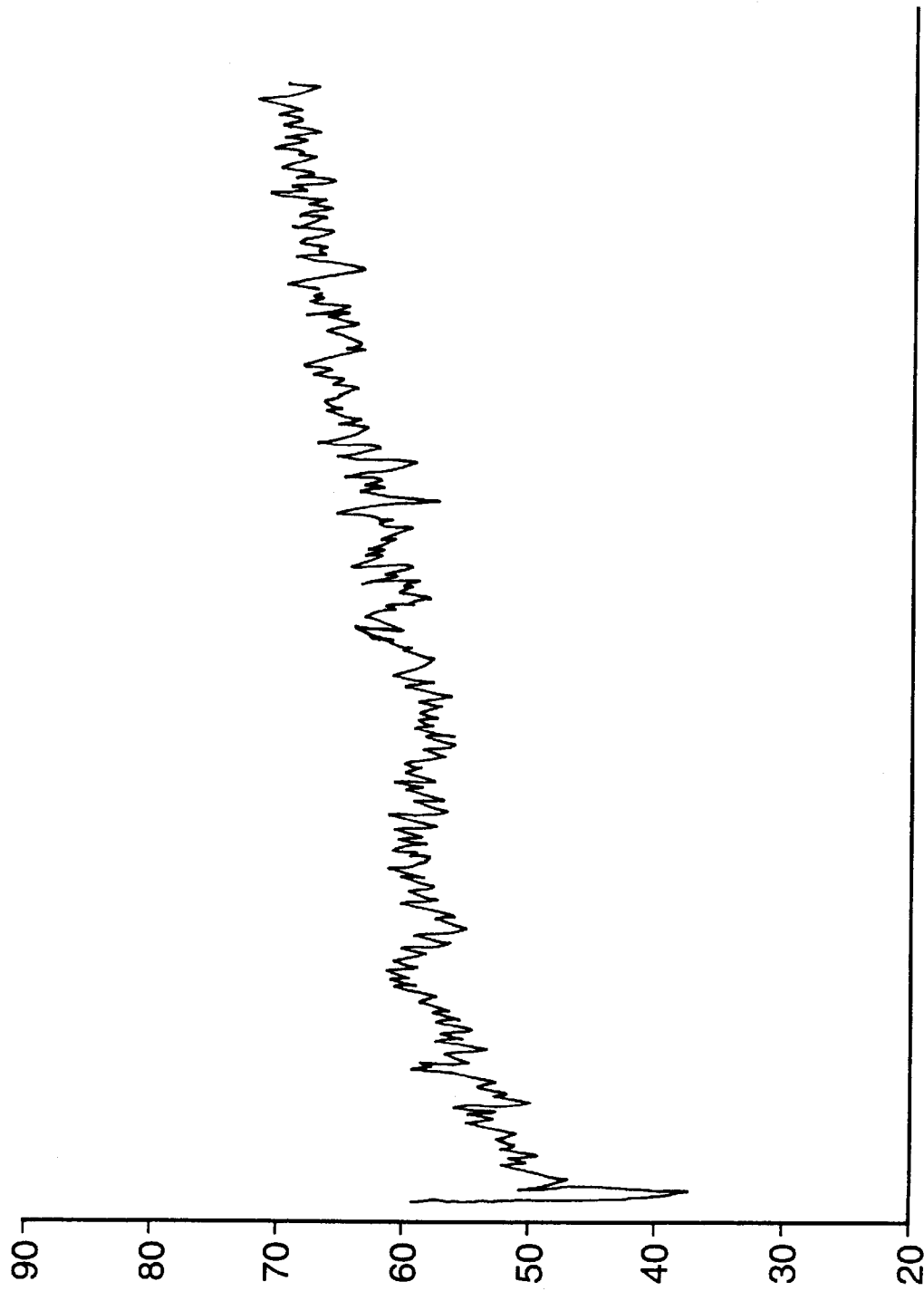
Figure 5:
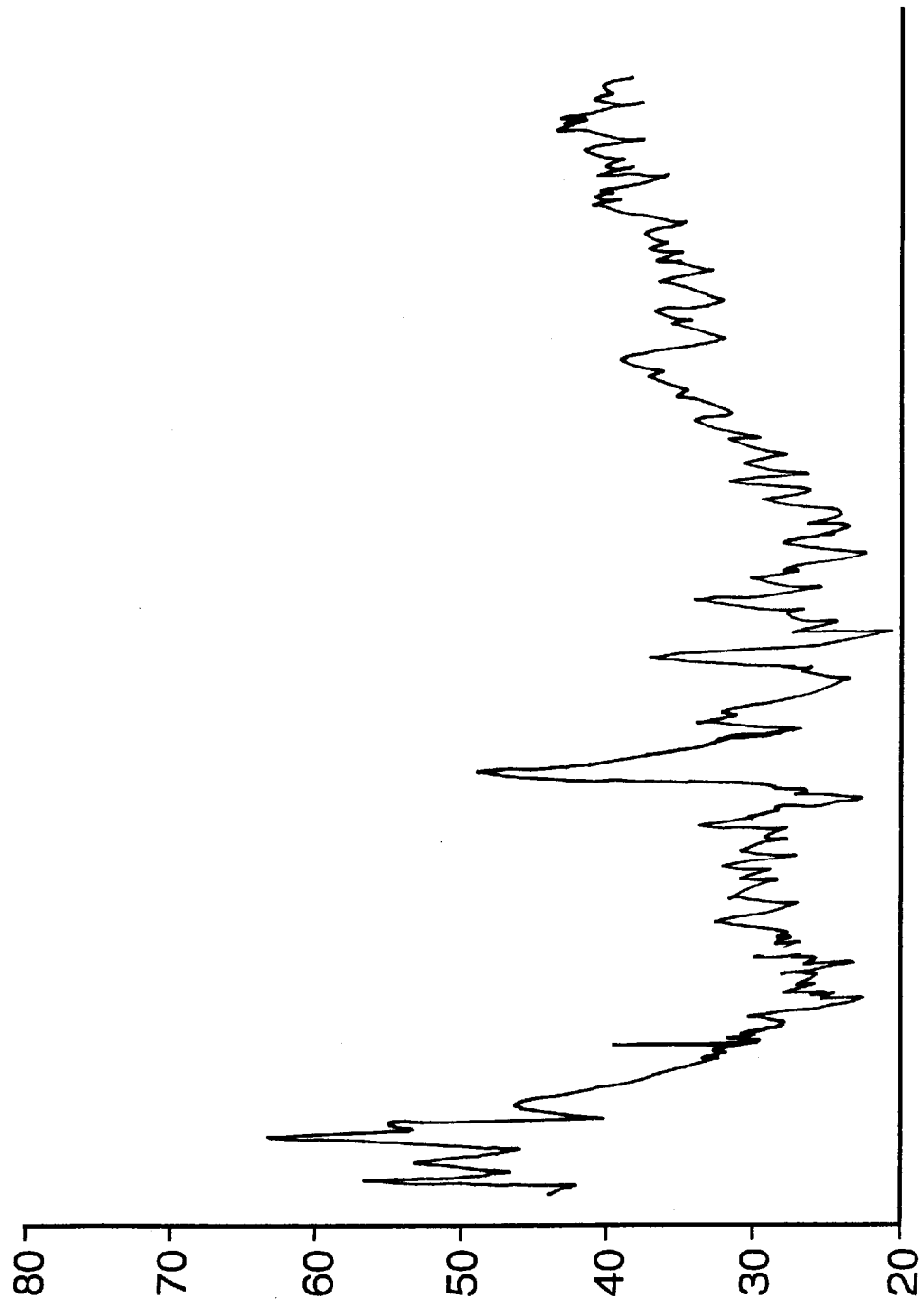
Figure 6:
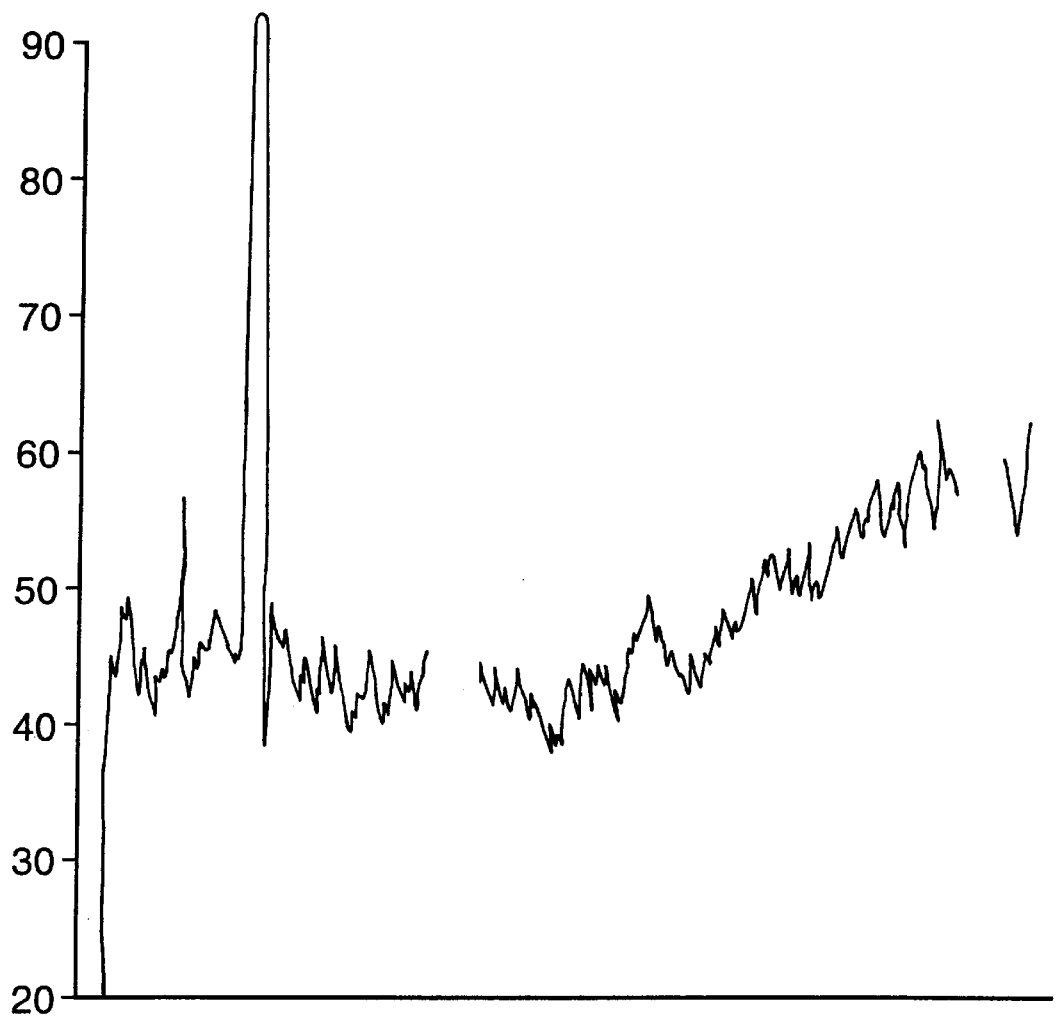
Figure 7:
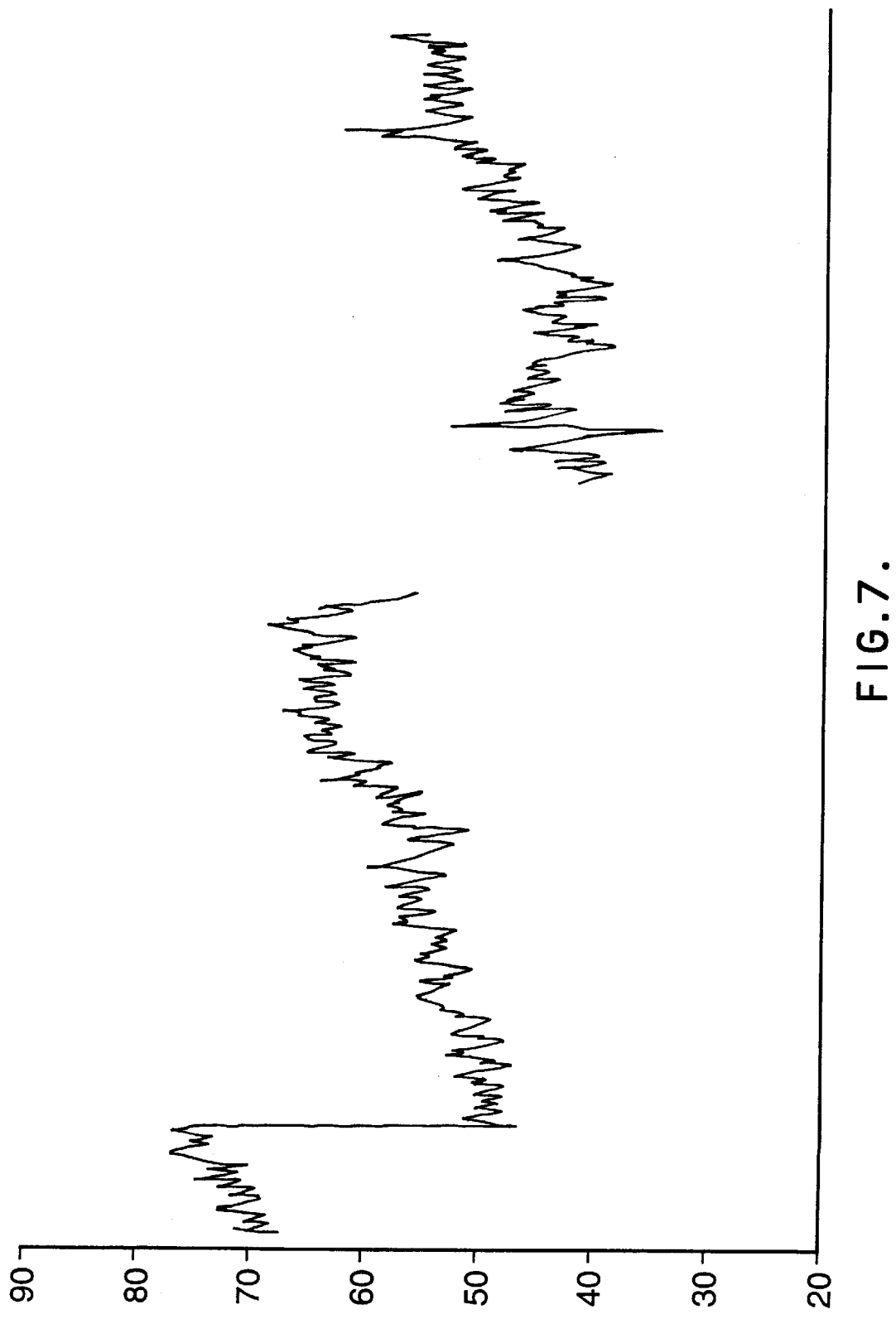
Figure 8:
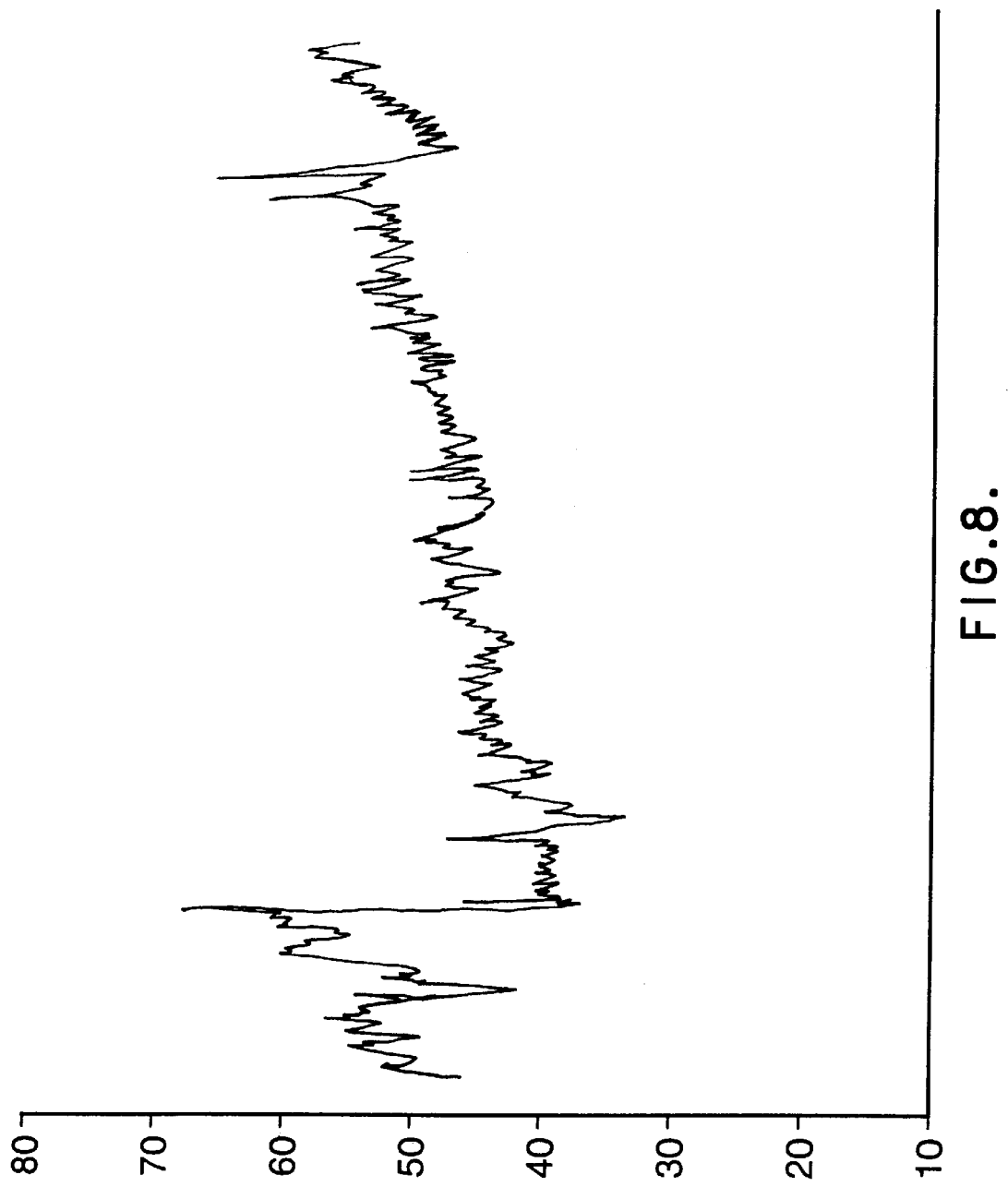

| | |
|---|---|
| FIG. 2 | PBT(50)B, 10 CHROM.Response. to HD |
| FIG. 3 | PGT 100 CHROM (700)B. Response to HD |
| FIG. 4 | RLM. Response to AP. No further change in slope with AD |
| FIG. 5 | CHROM. Response to TEST in presence of NADPH. |
| FIG. 6 | RLM. Response to ORN in presence of NADPH |
| FIG. 7 | RLM + N. Two responses to HD, short latency in both. |
| FIG. 8 | RLM. Slight response to ORN. Enhanced slope with HD. |

TABLE 4-continued

Legends to Figures

Figure 9:
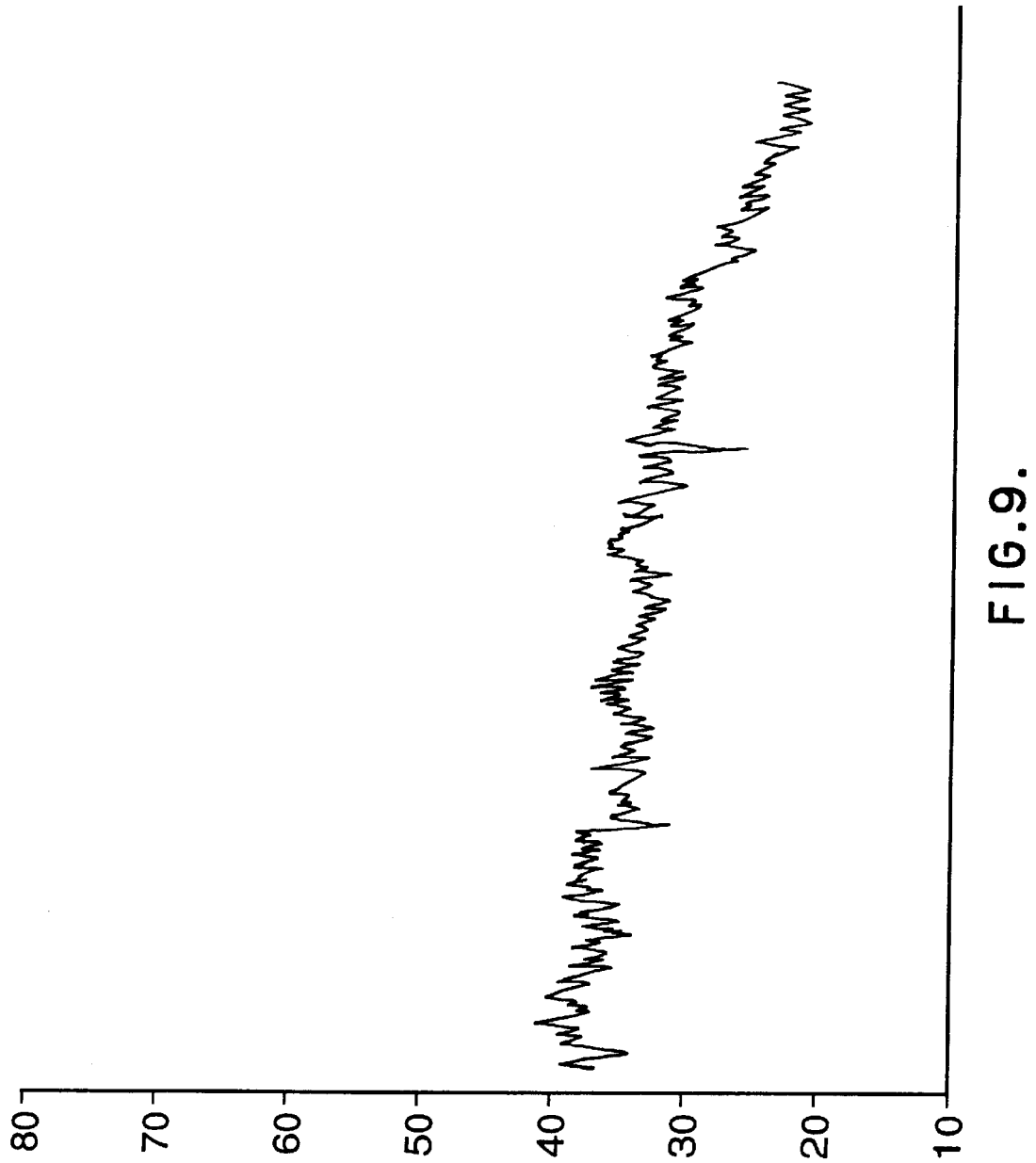
Figure 10:
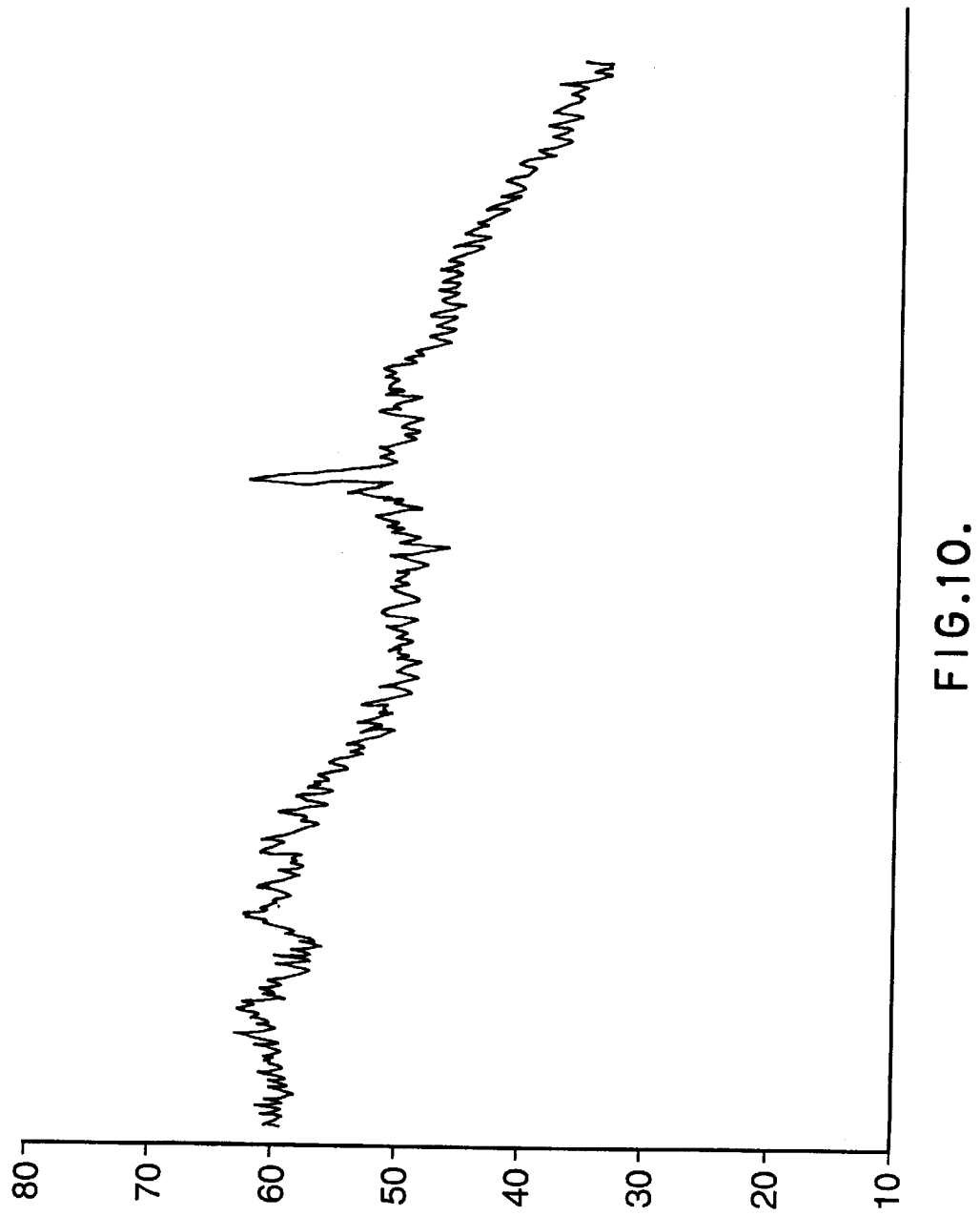
Figure 11:
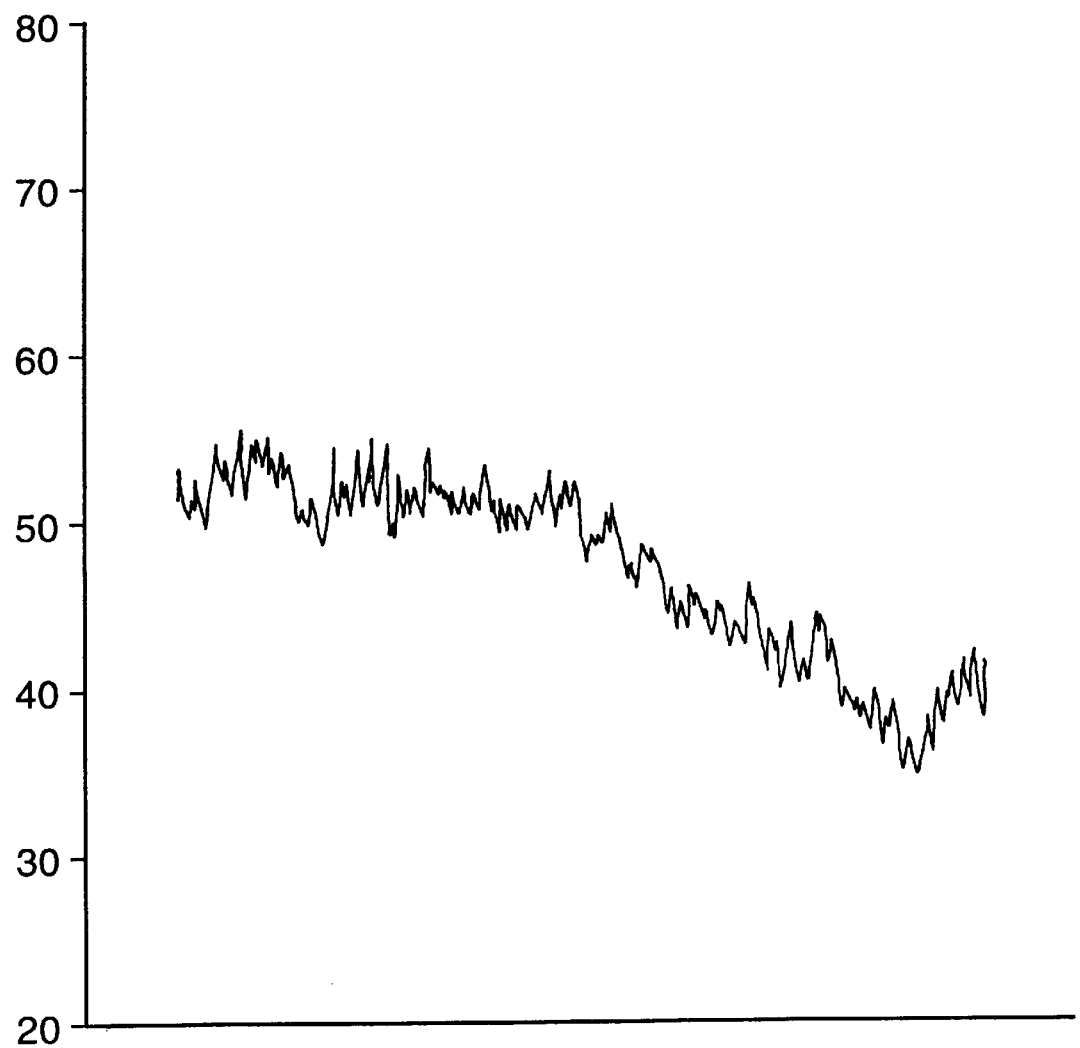
Figure 12:
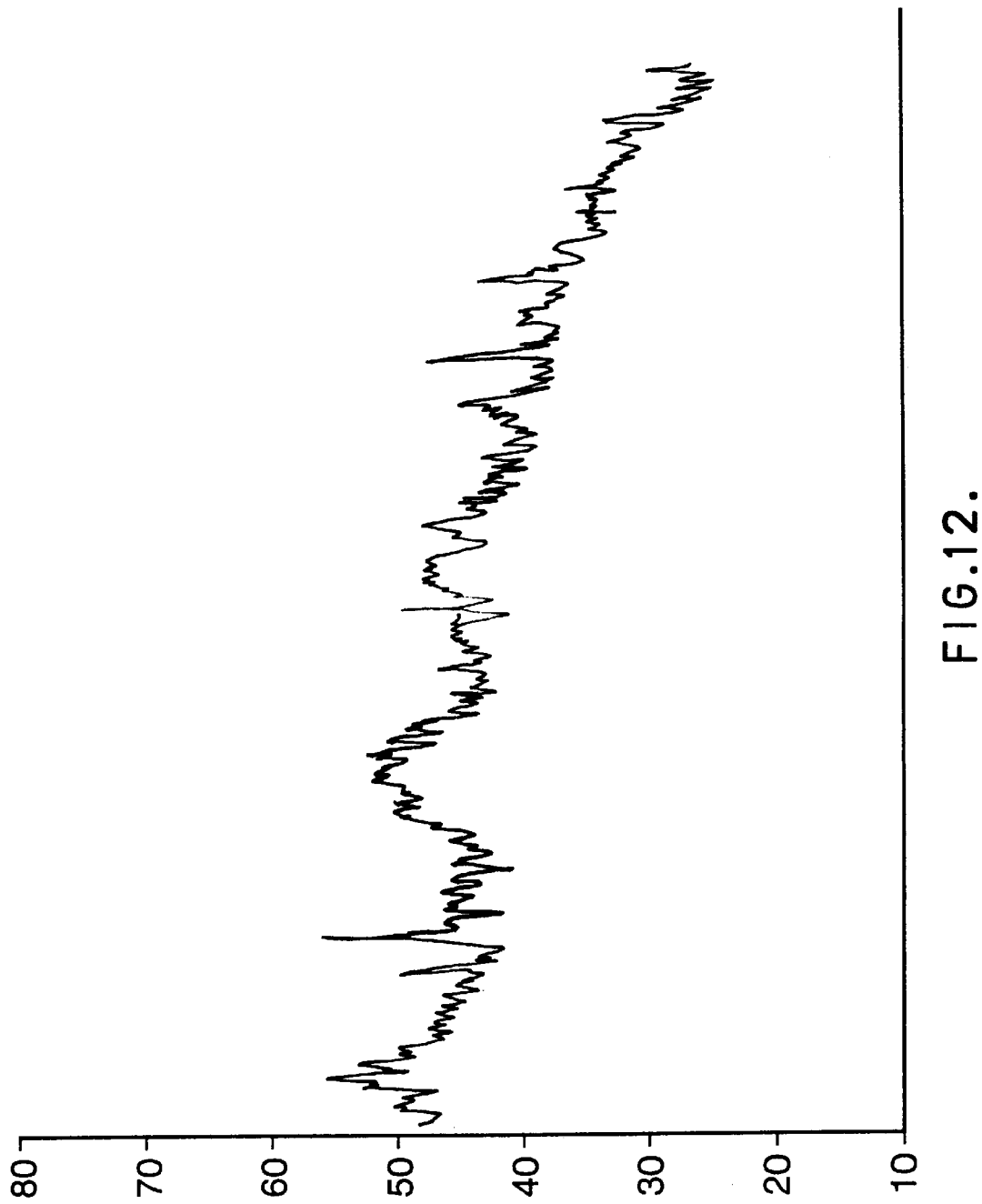
Figure 13:
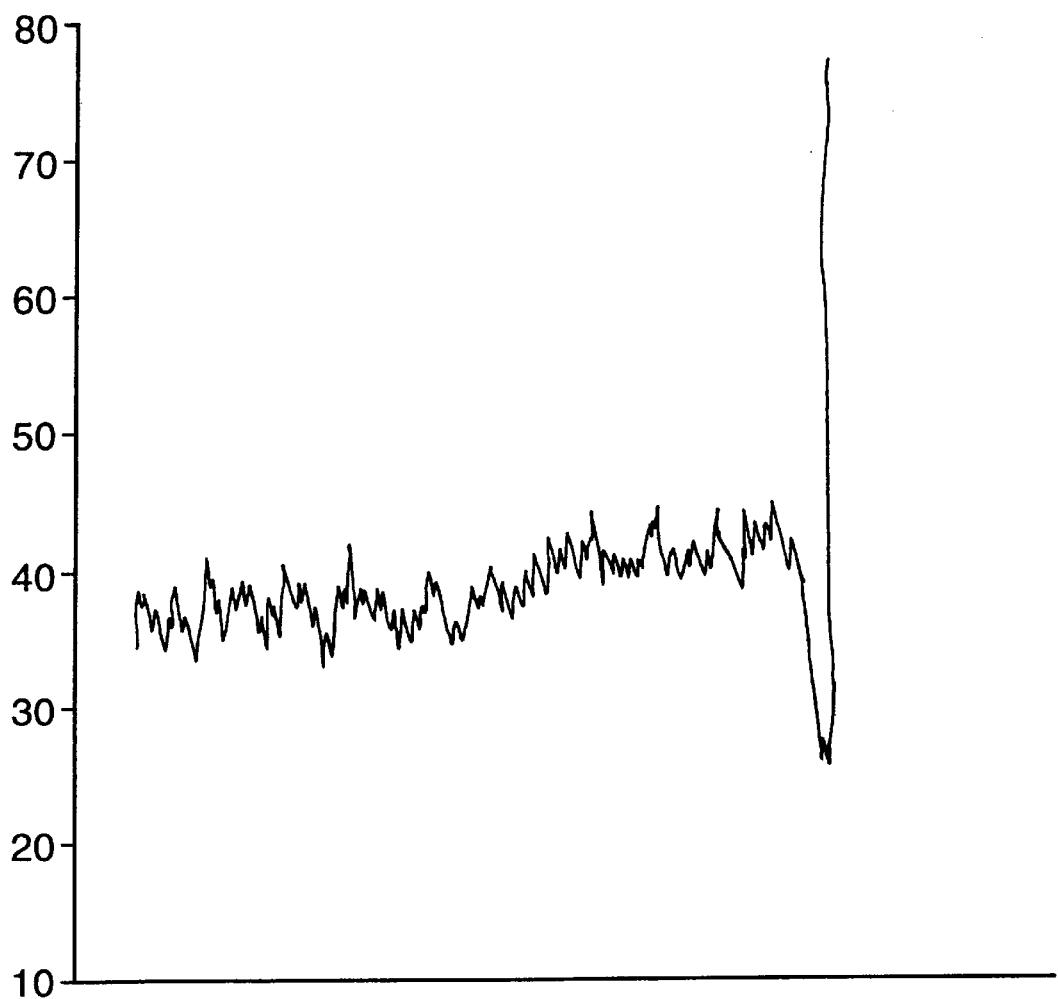
Figure 14:
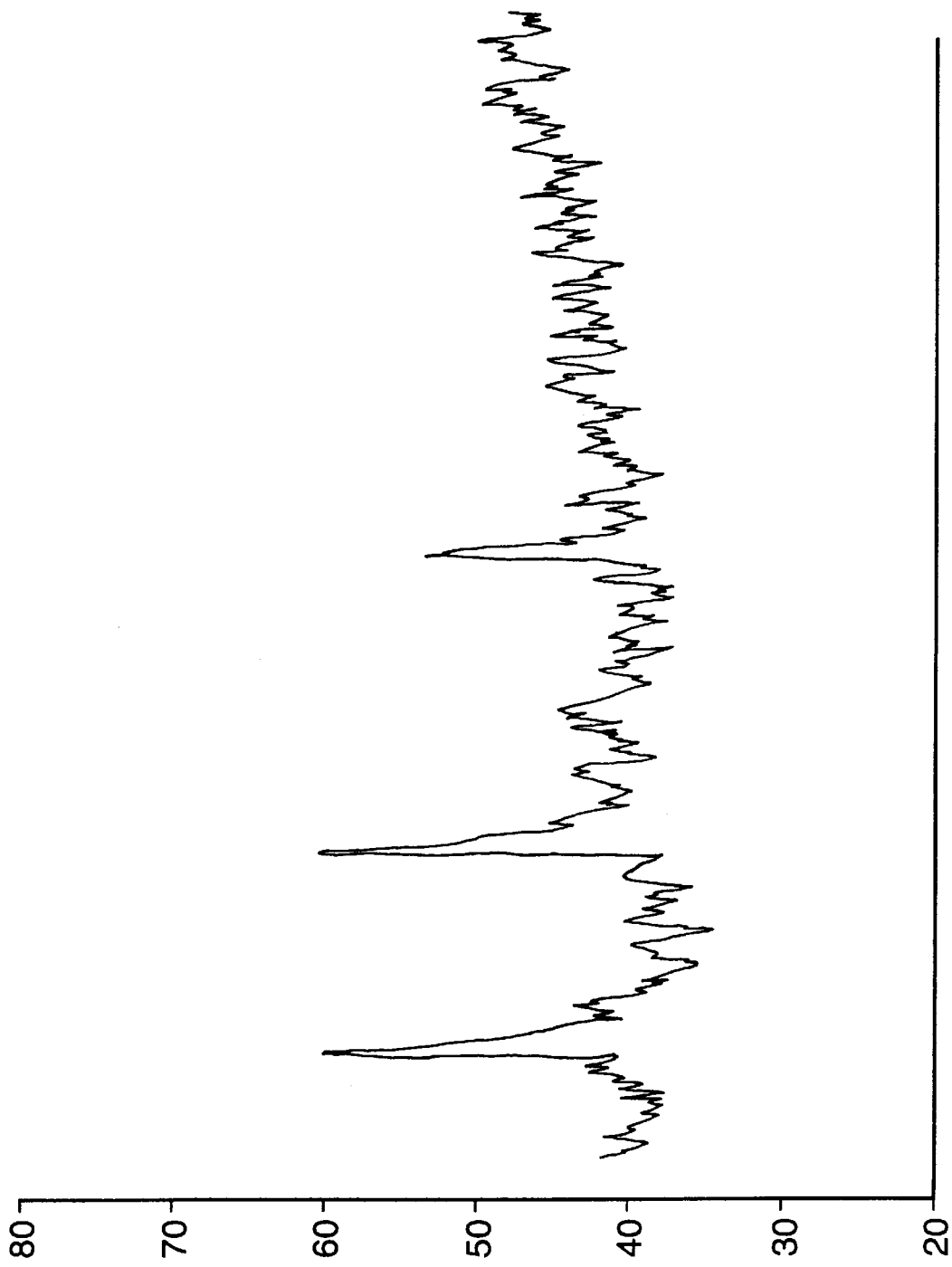
Figure 15:
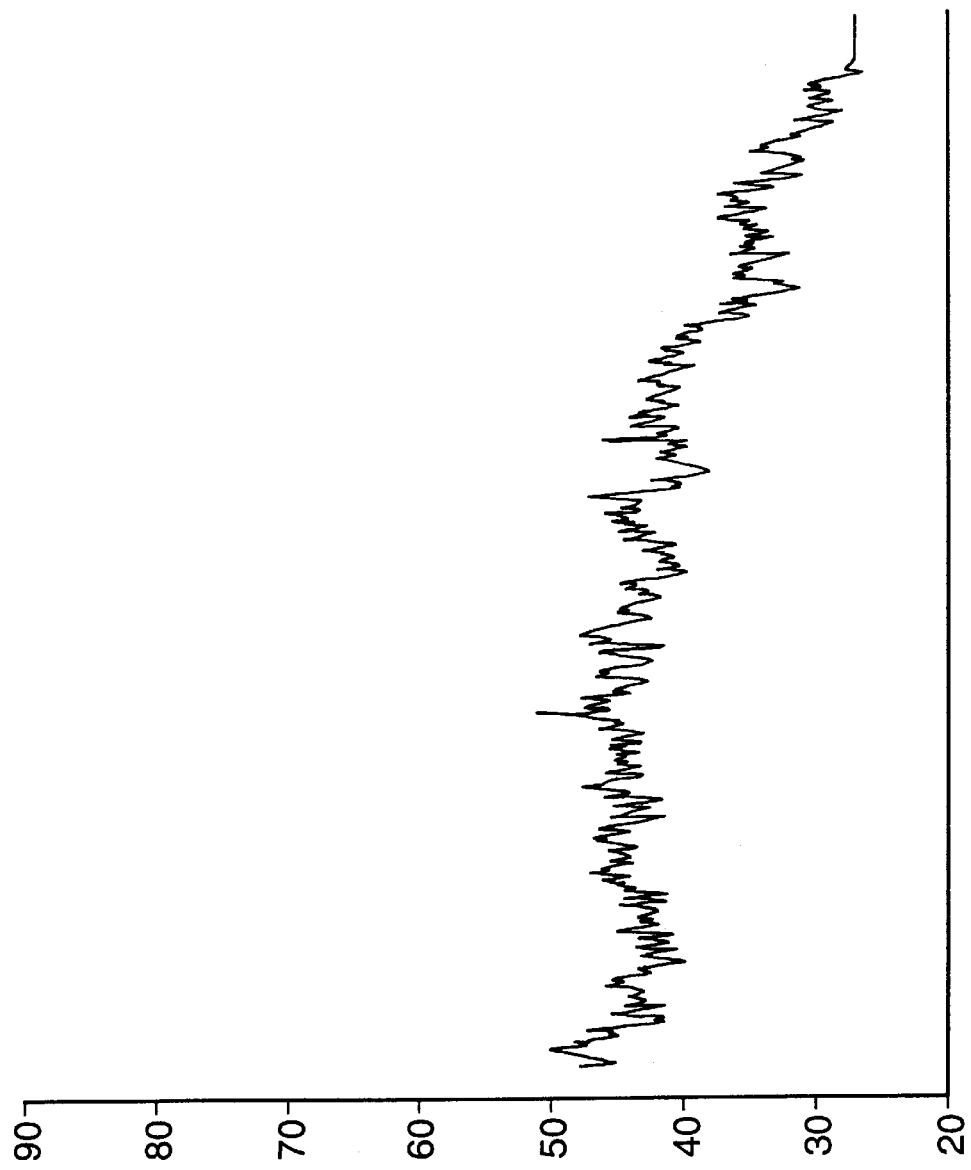
Figure 16:
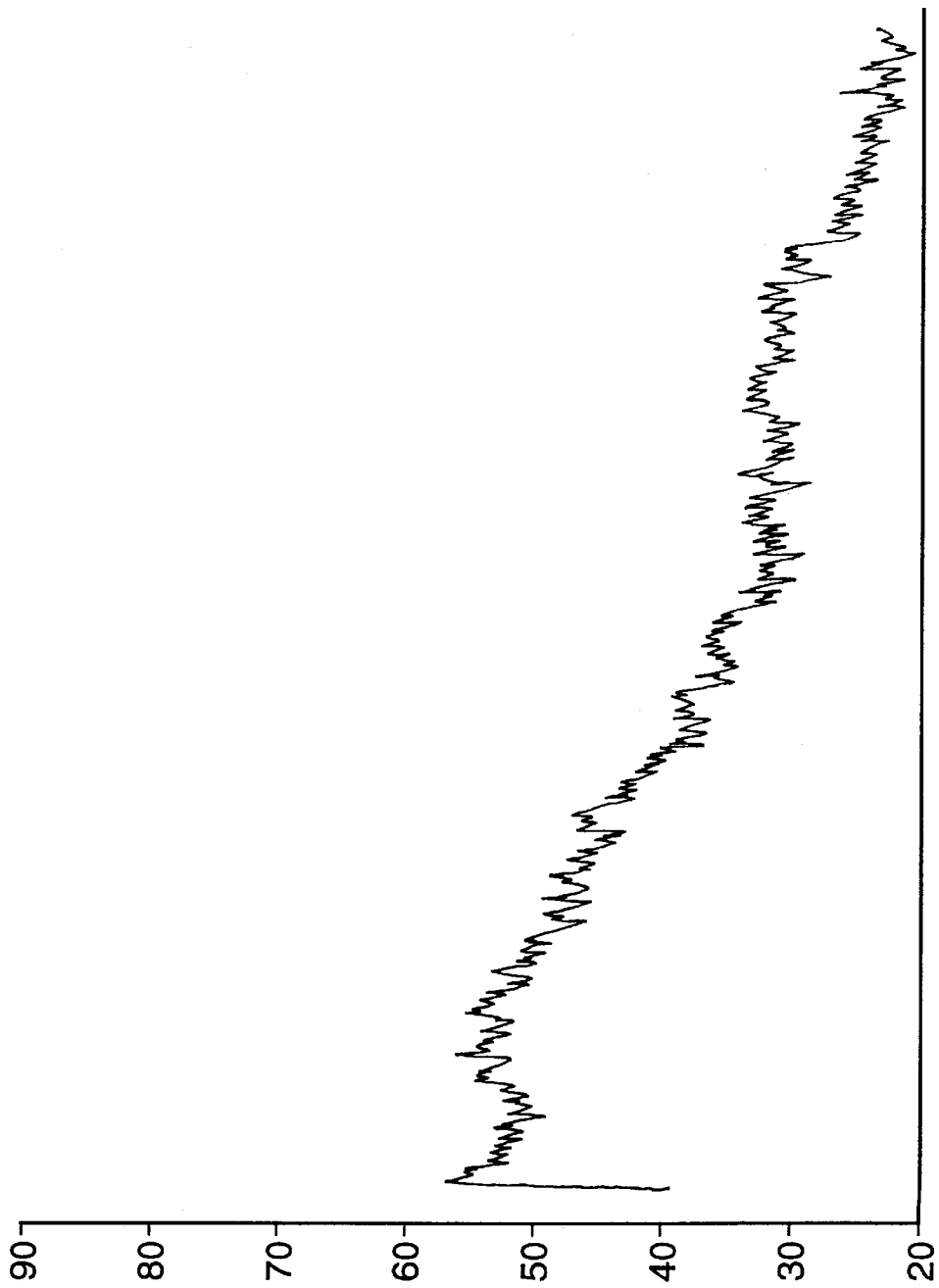
Figure 17:
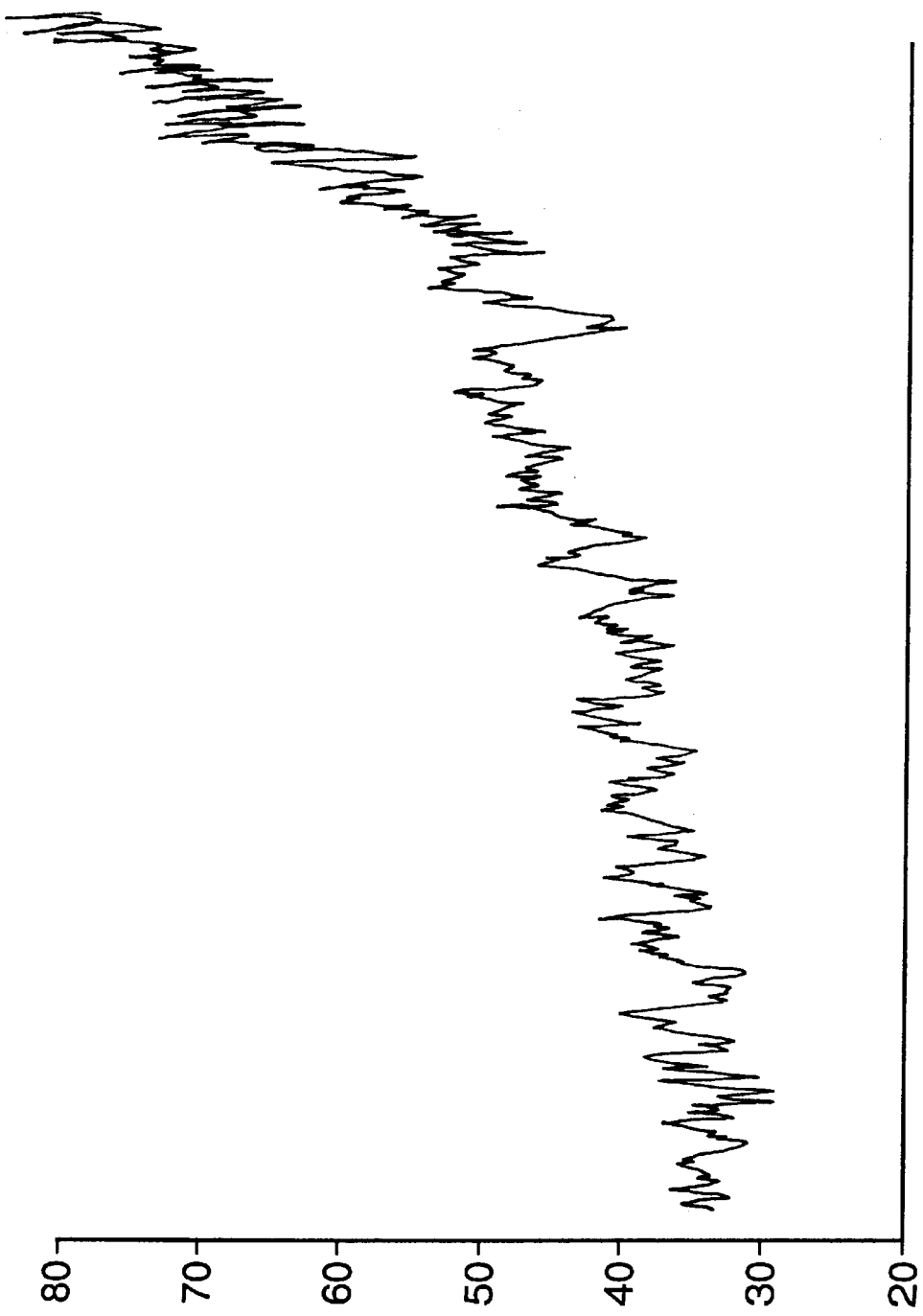
Figure 18:
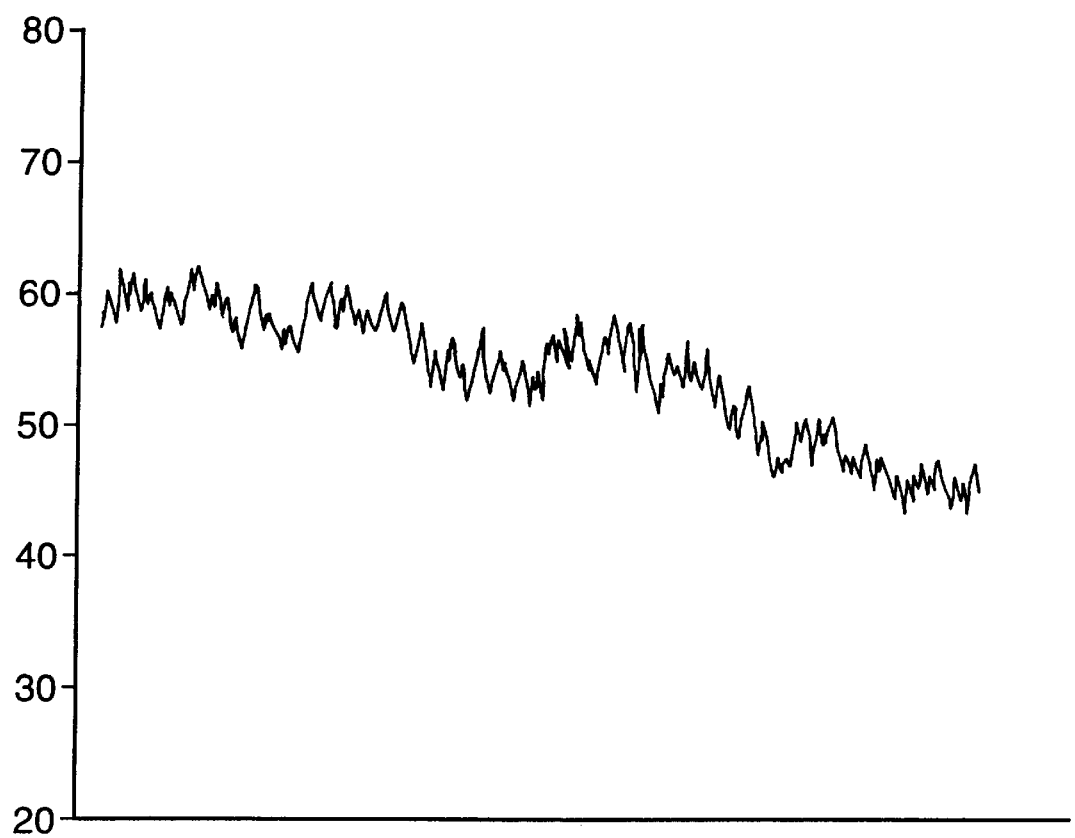
Figure 19:
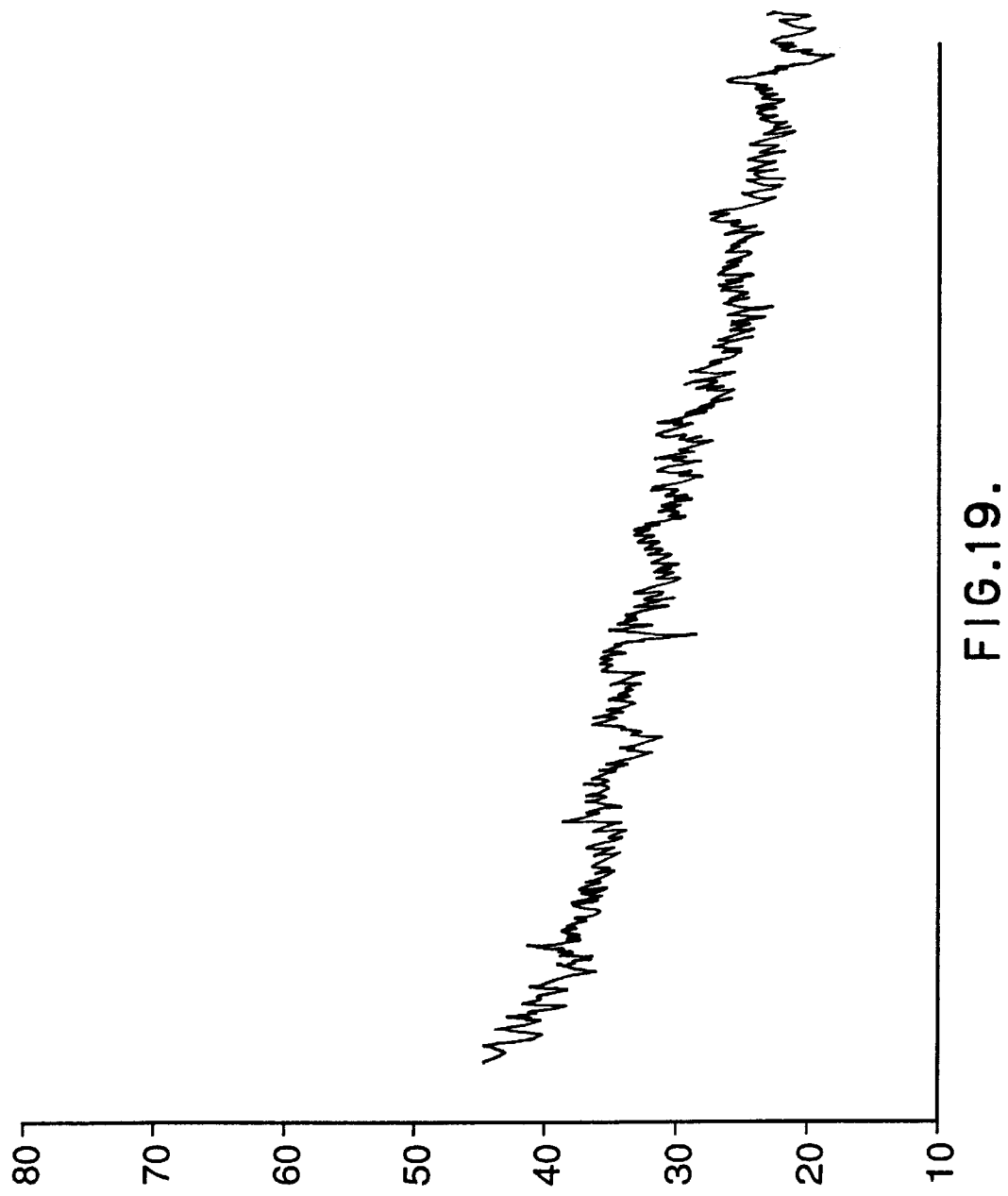
Figure 20:
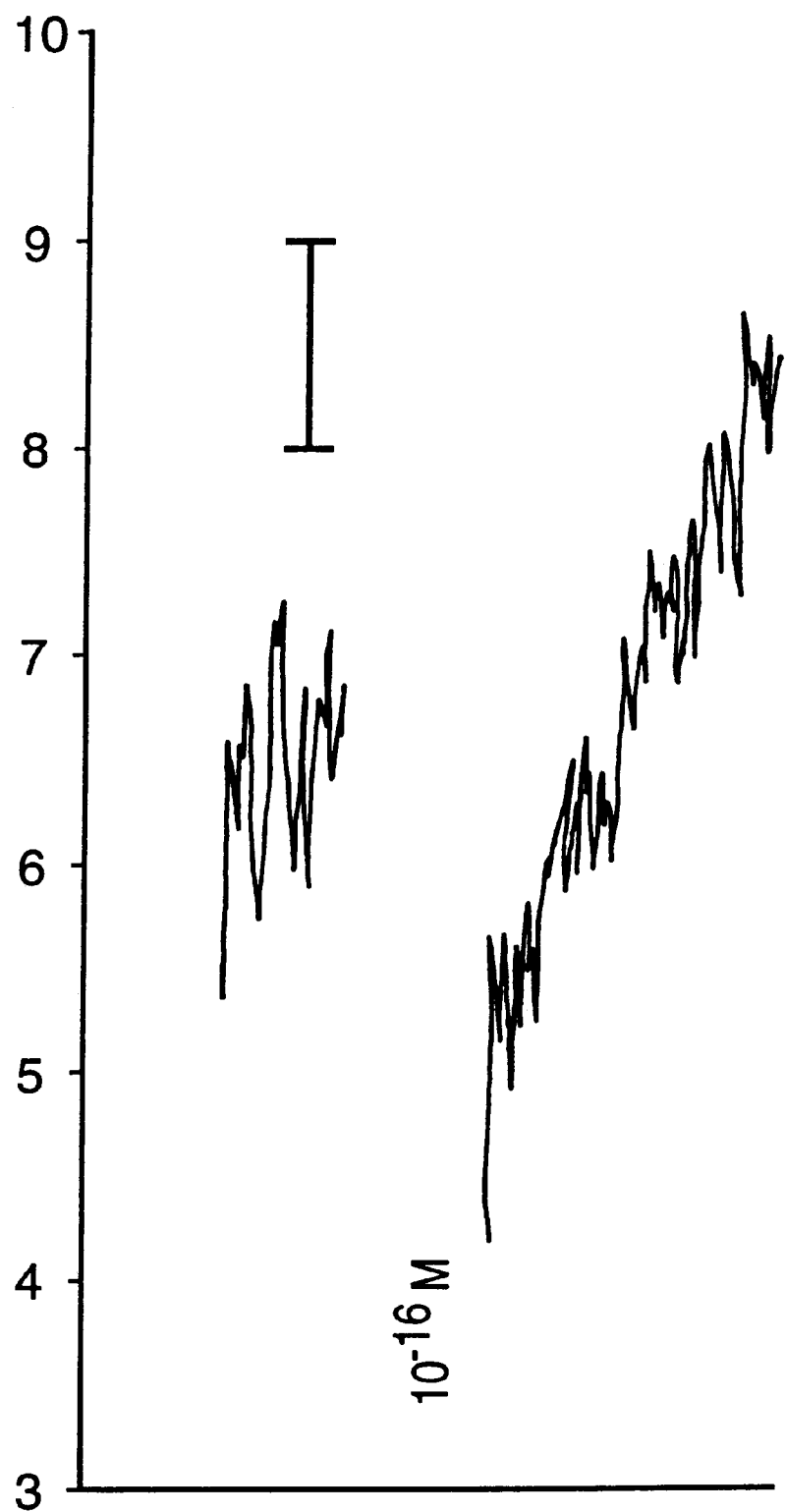
Figure 21:
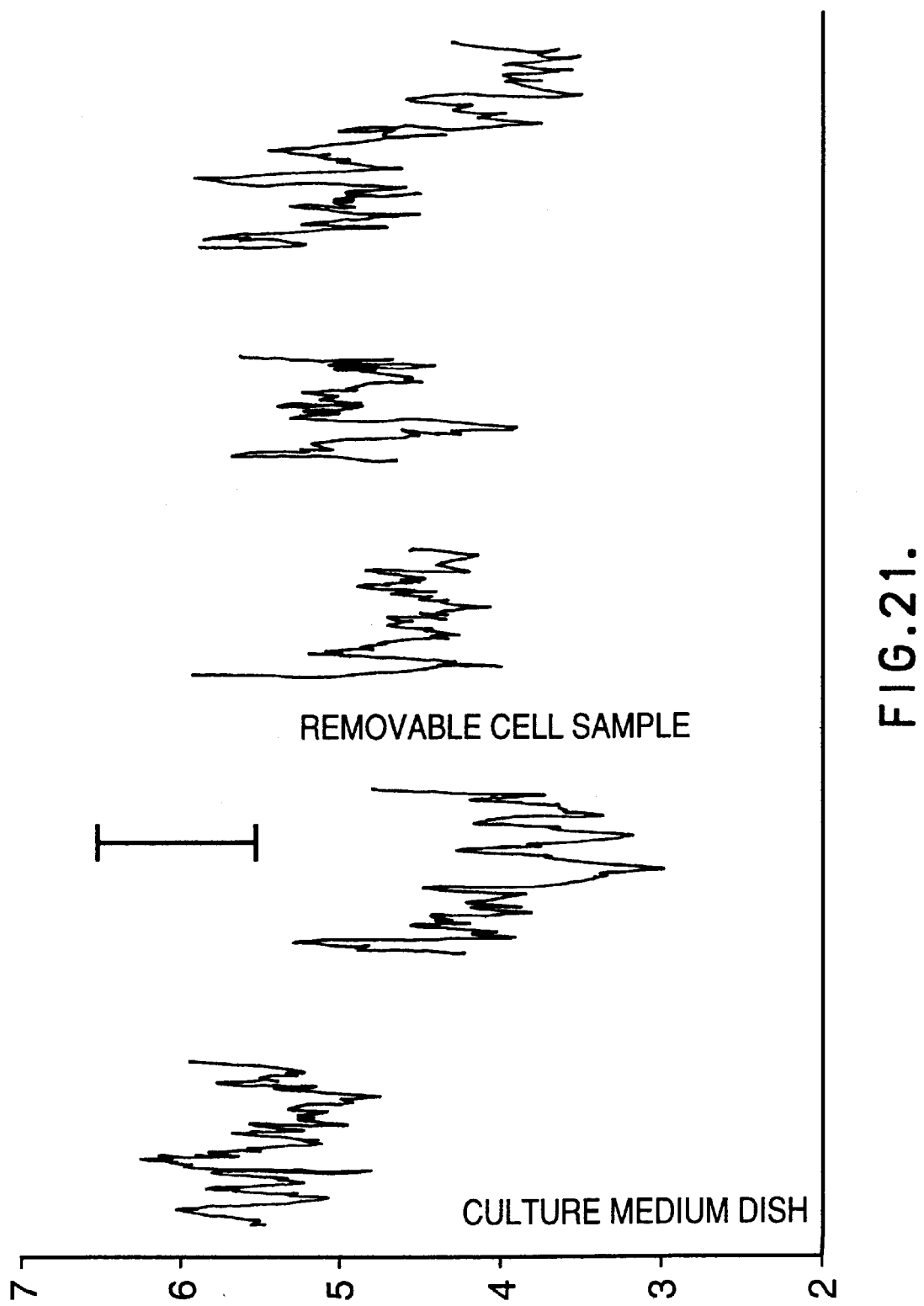
Figure 22:
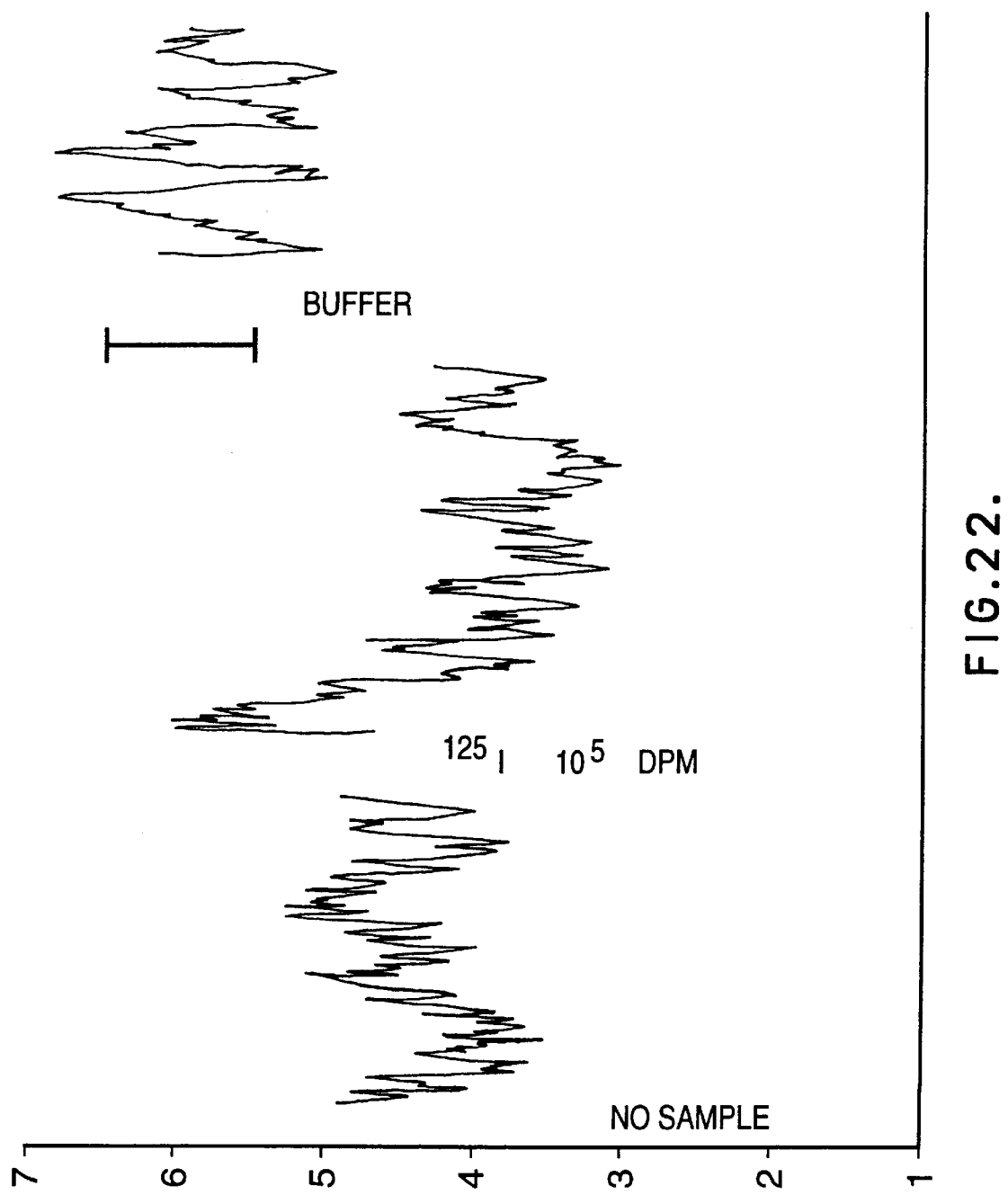
Figure 23:
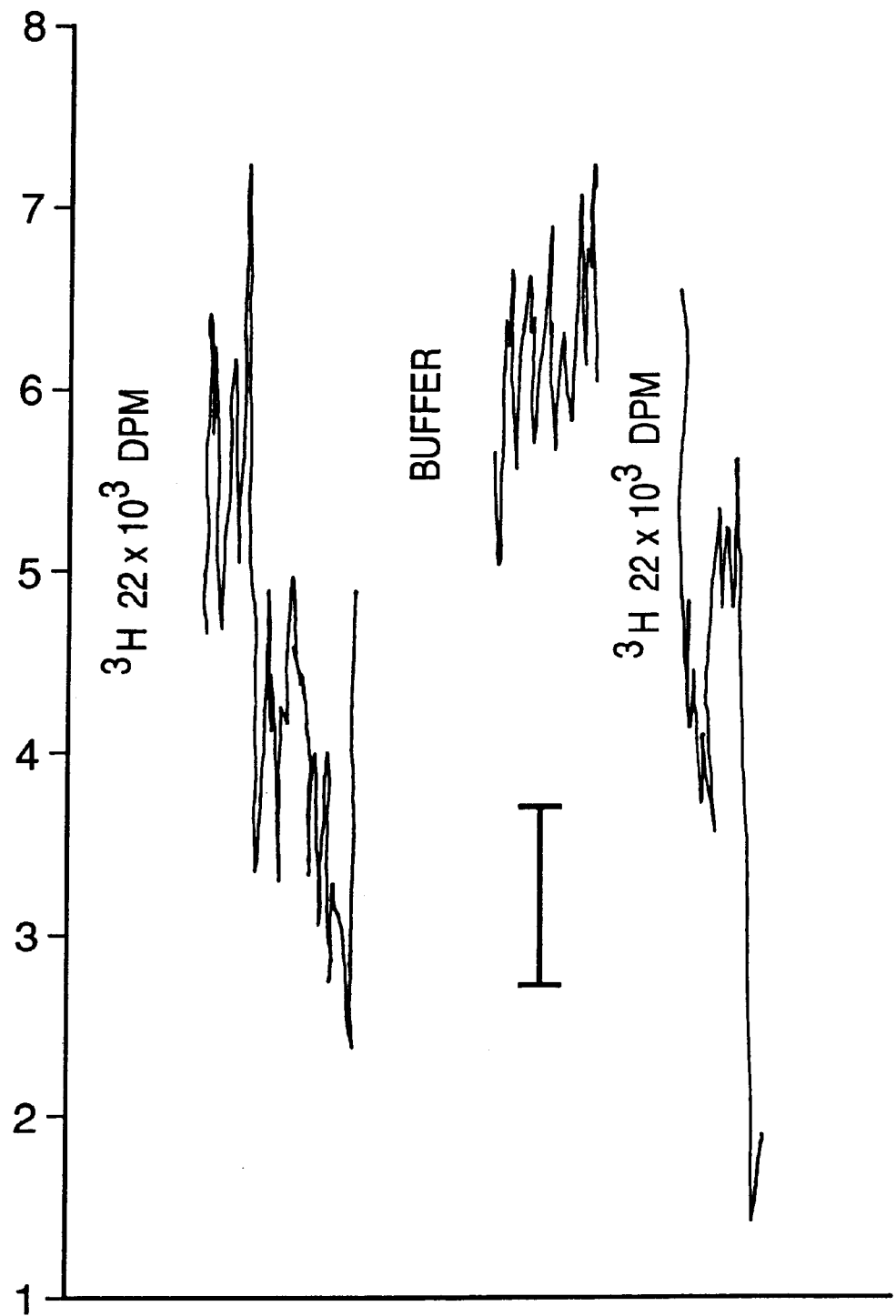

| | |
|---|---|
| | PU(10) N(10) response seen at end of record. |
| FIG. 9 | RLM + N. Response to AN |
| FIG. 10 | RLM. No response to ORN (unusual). No response to N. Response to PU. |
| FIG. 11 | CHROM. Response to ORN |
| FIG. 12 | Phospholipid/Buffer. Addition of PLase ("50 enzyme", on record) generates response |
| FIG. 13 | CHROM. Response to Regen |
| FIG. 14 | PL/Buffer. Response to purified bee venom PLase |
| FIG. 15 | PLN. Response to HD |
| FIG. 16 | CHROM. No response to fluoxetine (0.2 mil; "prozac", on record) until NADPH added |
| FIG. 17 | RLM. Response to HOL ("H˙ol" on record) |
| FIG. 18 | RLM + N. Response to AP. Increased slope with PUTR |
| FIG. 19 | PLN. No response to PUTR until NADPH added |
| FIG. 20 | Non-active sample is 1500 µL ORN buffer as thin film. E180K (on.record) is P450 isoenzyme, $10^{-16}$M (estimated as 0.1% of total protein), thin film. |
| FIG. 21 | Thin film suspension of rat liver whole cells. Same 50 cells each trial. Control responses are from culture medium |
| FIG. 22 | $^{125}$I(NaI), ca $10^5$ DPM |
| FIG. 23 | Tritium (uniformly labelled 3H-histamine), ca. $22 \times 10^3$ DPM |

Calibrations:
Unless otherwise stated, vertical deflection. of one major division (accented lines parallel to long axis of record) represents approximately 50 microgauss at the magnetosensitive region of the Hall-effect magnetometer probe In FIGS. 20 to 23, all samples were remote from probe-reaction vessel assembly; calibrations both represent 50 microgauss at magnetometer probe Hall-effect region.

What is claimed is:

1. A method of detection of an unknown event in which electron translation is accompanied by photon emission, which comprises:
    detecting changes in electromagnetic field strength, the electromagnetic field being produced by atomically- or molecularly-generated magnetic fields, said changes being caused by photon emission accompanying electron translation in the unknown event;
    recording a time course of said changes in electromagnetic field strength; and
    comparing said recorded time course with predetermined time courses of changes in electromagnetic field strength of known events in which electron translation is accompanied by photon emission so as to determine the cause of the unknown event.

2. The method of claim 1 wherein said event comprises a chemical reaction, a molecular interaction and/or a change of state of matter.

3. The method of claim 2, wherein said event is an enzyme reaction and the electromagnetic consequences of such enzyme reaction are detected and measured from samples at temperatures which are optimum for the enzyme reaction of interest.

4. The method of claim 1 wherein said analysis is effected by FAST FOURIER TRANSFORM (FFT) procedures.

5. The method of claim 4 wherein said PFT procedures are enhanced, augmented and/or assisted by at least one other form of signal analysis.

6. The method of claim 5 wherein said other forms of signal analysis is pattern recognition and/or wave trend forecasting.

7. The method of claim 1 wherein said changes in electromagnetic field strength are detected by a magnetometer capable of generating an electrical signal of strength proportional to the electromagnetic field strength produced by the event.

8. The method of claim 7 wherein said change in electromagnetic field strength is recorded by recording the change in strength of the electrical signal produced by the magnetometer.

9. An apparatus for detecting and recording an unknown event in which electron translation is accompanied by photon emission, which comprises:

magnetometer means for generating an electrical signal of strength proportional to changes in electromagnetic field produced by atomically- or molecularly-generated fields, said changes being produced by the unknown event in which electron transmission is accompanied by photon emission, recording means for recording a time course of said electrical signal produced by said magnetometer means and a period of time for which said electrical signal is produced by said unknown event; and analysis means for analyzing a time course of said electrical signal recorded by said recording means and for comparing said recorded time course with predetermined time courses of changes in electromagnetic field strengths of known events in which electron translation is accompanied by photon emission so as to determine the cause of the unknown event.

10. The apparatus of claim 8 wherein said magnetometer means is a Hall-effect probe.

11. The apparatus of claim 9 wherein said magnetometer means is a superconducting quantum-interference detector probe.

* * * * *